(12) United States Patent
Gerber

(10) Patent No.: US 9,993,639 B2
(45) Date of Patent: Jun. 12, 2018

(54) IMPLANTABLE MEDICAL ELONGATED MEMBER INCLUDING A TISSUE RECEIVING FIXATION CAVITY

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1712 days.

(21) Appl. No.: 11/591,294

(22) Filed: Oct. 31, 2006

(65) Prior Publication Data

US 2008/0103577 A1 May 1, 2008

(51) Int. Cl.
| | |
|---|---|
| *A61N 1/05* | (2006.01) |
| *H04N 7/173* | (2011.01) |
| *H04N 21/235* | (2011.01) |
| *H04N 21/434* | (2011.01) |
| *H04N 21/435* | (2011.01) |
| *H04N 21/4782* | (2011.01) |
| *H04N 21/482* | (2011.01) |
| *H04N 21/858* | (2011.01) |

(52) U.S. Cl.
CPC ......... *A61N 1/0529* (2013.01); *A61N 1/0534* (2013.01); *A61N 1/0539* (2013.01); *A61N 1/0551* (2013.01); *H04N 7/17318* (2013.01); *H04N 21/235* (2013.01); *H04N 21/435* (2013.01); *H04N 21/4348* (2013.01); *H04N 21/4782* (2013.01); *H04N 21/482* (2013.01); *H04N 21/8586* (2013.01); *A61N 1/0536* (2013.01); *A61N 1/0558* (2013.01)

(58) Field of Classification Search
CPC ..... A61M 25/0015; A61B 2017/00477; A61B 5/6882; A61B 2017/306
USPC .......... 607/116, 149; 600/309, 561
See application file for complete search history.

(56) References Cited

U.S. PATENT DOCUMENTS

| | | | |
|---|---|---|---|
| 5,139,033 A | 8/1992 | Everett et al. | |
| 5,336,252 A | 8/1994 | Cohen | |
| 5,827,216 A | * 10/1998 | Igo et al. | ........................ 604/21 |
| 6,162,195 A | 12/2000 | Igo et al. | |

(Continued)

FOREIGN PATENT DOCUMENTS

| | | |
|---|---|---|
| WO | WO 00/59376 | 10/2000 |
| WO | WO 02/087657 A2 | 11/2002 |

(Continued)

OTHER PUBLICATIONS

Notification of Transmittal of the International Preliminary Report on Patentability dated Oct. 14, 2008 for PCT Application No. PCT/US2007/001958 (10 pgs.).

(Continued)

*Primary Examiner* — Michael D Abreu
(74) *Attorney, Agent, or Firm* — Shumaker & Sieffert, P.A.

(57) ABSTRACT

This disclosure describes techniques for securing an elongated member, such as a medical lead, within a tissue of a patient. In particular, suction is applied from a vacuum to a vacuum cavity located proximate to a distal end of the lead to draw in tissue from the target therapy delivery site to the vacuum cavity. A fixation element is coupled to the tissue within the vacuum cavity to fix the lead to the target therapy delivery site. The fixation techniques of this disclosure secure the medical lead to the tissue of the patient to prevent the medical lead from migrating away from the target tissue location.

24 Claims, 12 Drawing Sheets

(56) References Cited

U.S. PATENT DOCUMENTS

| | | |
|---|---|---|
| 6,285,897 B1 | 9/2001 | Kilcoyne et al. |
| 6,514,250 B1 | 2/2003 | Jahns et al. |
| 6,535,764 B2 | 3/2003 | Imran et al. |
| 6,542,776 B1 | 4/2003 | Gordon et al. |
| 6,666,844 B1 | 12/2003 | Igo et al. |
| 6,684,104 B2 | 1/2004 | Gordon et al. |
| 6,689,056 B1 | 2/2004 | Kilcoyne et al. |
| 6,754,536 B2 | 6/2004 | Swoyer et al. |
| 6,960,205 B2 | 11/2005 | Jahns et al. |
| 6,978,176 B2 | 12/2005 | Lattouf |
| 7,076,305 B2 | 7/2006 | Imran et al. |
| 2002/0103424 A1 | 8/2002 | Swoyer et al. |
| 2003/0045919 A1 | 3/2003 | Swoyer et al. |
| 2003/0078575 A1* | 4/2003 | Jahns et al. ............ 606/41 |
| 2003/0212446 A1 | 11/2003 | Kaplan et al. |
| 2004/0088023 A1 | 5/2004 | Imran et al. |
| 2004/0133089 A1 | 7/2004 | Kilcoyne et al. |
| 2004/0147976 A1 | 7/2004 | Gordon et al. |
| 2004/0158138 A1 | 8/2004 | Kilcoyne et al. |
| 2004/0215128 A1 | 10/2004 | Eerdmans |
| 2004/0243211 A1* | 12/2004 | Colliou et al. ............ 607/133 |
| 2004/0260164 A1 | 12/2004 | Kilcoyne et al. |
| 2005/0043601 A1 | 2/2005 | Kilcoyne et al. |
| 2005/0090873 A1 | 4/2005 | Imran |
| 2005/0102003 A1 | 5/2005 | Grabek et al. |
| 2005/0177220 A1 | 8/2005 | Iaizzo et al. |
| 2005/0209653 A1 | 9/2005 | Herbert et al. |
| 2005/0222537 A1 | 10/2005 | Dinsmoor et al. |
| 2005/0245840 A1* | 11/2005 | Christopherson et al. ... 600/561 |
| 2006/0089690 A1 | 4/2006 | Gerber |

FOREIGN PATENT DOCUMENTS

| | | |
|---|---|---|
| WO | WO 2004/002288 A2 | 1/2004 |
| WO | WO 2004/041349 A1 | 5/2004 |
| WO | WO 2004/045675 A2 | 6/2004 |
| WO | WO 2005/016157 A1 | 2/2005 |
| WO | WO 2005/044079 A2 | 5/2005 |
| WO | WO 2005/077266 A1 | 8/2005 |

OTHER PUBLICATIONS

Reply to Written Opinion dated Jun. 5, 2008 for PCT Application No. PCT/US2007/001958 (16 pgs.).

Notification of Transmittal of the International Search Report and the Written Opinion of the International Searching Authority, or the Declaration for corresponding PCT Application No. PCT/US2007/001958, dated Jul. 5, 2006 (12 pgs.).

Response for European Application No. 07749196.7. received by the European Patent Office on Nov. 7, 2011. (12 pgs.).

Office Action dated Jun. 27, 2011 for European Application No. 07749196.7, (3 pgs.).

* cited by examiner

IMPLANTABLE MEDICAL ELONGATED MEMBER INCLUDING A TISSUE RECEIVING FIXATION CAVITY

TECHNICAL FIELD

This disclosure relates to medical device systems, and more particularly, to elongated members configured to deliver a therapy in a medical device system.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. An electrical stimulation system typically includes one or more implantable medical leads coupled to an external or implantable electrical stimulator.

The implantable medical lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, stomach, bladder, or within a brain or other organ of a patient, or within a muscle or muscle group of a patient. The one or more electrodes located proximate to the target stimulation site may deliver electrical stimulation therapy to the target stimulation site in the form electrical signals.

Electrical stimulation of a sacral nerve may eliminate or reduce some pelvic floor disorders by influencing the behavior of the relevant structures, such as the bladder, sphincter and pelvic floor muscles. Pelvic floor disorders include urinary incontinence, urinary urge/frequency, urinary retention, pelvic pain, bowel dysfunction, and male and female sexual dysfunction. The organs involved in bladder, bowel, and sexual function receive much of their control via the second, third, and fourth sacral nerves, commonly referred to as S2, S3 and S4 respectively. Thus, in order to deliver electrical stimulation to at least one of the S2, S3, or S4 sacral nerves, an implantable medical lead is implanted proximate to the sacral nerve(s).

Electrical stimulation of a peripheral nerve, such as stimulation of an occipital nerve, may be used to mask a patient's feeling of pain with a tingling sensation, referred to as paresthesia. Occipital nerves, such as a lesser occipital nerve, greater occipital nerve or third occipital nerve, exit the spinal cord at the cervical region, extend upward and toward the sides of the head, and pass through muscle and fascia to the scalp. Pain caused by an occipital nerve, e.g. occipital neuralgia, may be treated by implanting a lead proximate to the occipital nerve to deliver stimulation therapy.

In many electrical stimulation applications, it is desirable for a stimulation lead to resist migration following implantation. For example, it may be desirable for the electrodes disposed at a distal end of the implantable medical lead to remain proximate to a target stimulation site in order to provide adequate and reliable stimulation of the target stimulation site. In some applications, it may also be desirable for the electrodes to remain substantially fixed in order to maintain a minimum distance between the electrode and a nerve in order to help prevent inflammation to the nerve and in some cases, unintended nerve damage. Securing the implantable medical lead at the target stimulation site may minimize lead migration.

SUMMARY

This disclosure describes techniques for securing an implantable medical elongated member, such as a medical lead or catheter, within a tissue of a patient. The elongated member is configured to deliver a therapy, such as electrical stimulation, drug delivery, or both, from a medical device to a target therapy delivery site in the patient. The fixation mechanism/technique of this disclosure secures the elongated member to the tissue of the patient to prevent the elongated member from migrating away from the target therapy delivery site.

In particular, after the implantable medical elongated member implanted in a patient proximate to the target therapy delivery site, suction (i.e., vacuum pressure) is applied from a vacuum source to a vacuum cavity defined by the elongated member, thereby drawing tissue adjacent to the vacuum cavity into the vacuum cavity. The vacuum cavity may be in fluidic communication with the vacuum source through a vacuum channel that extends the length of the elongated member. The vacuum channel may be located in the elongated member itself or within an introducer and coupled to the vacuum cavity of the elongated member via a vacuum inlet. The elongated member further includes a fixation element disposed within a channel. After the vacuum cavity receives adjacent tissue, the fixation element is drawn into engagement with the tissue within the vacuum cavity in order to fix the elongated member to the target therapy delivery site. As an example, a pin may be driven through the tissue within the vacuum cavity to fix the elongated member to the target therapy delivery site.

In one embodiment, an implantable elongated member configured to deliver a therapy from a medical device to a target therapy delivery site in a patient comprises an elongated body extending between a proximal end configured to couple to the medical device and a distal end. The elongated body defines a vacuum cavity configured to receive vacuum pressure from a vacuum source to draw tissue of the patient into the vacuum cavity. The implantable elongated member further comprises a channel disposed within the elongated body and a fixation element disposed within the channel and configured to engage with the tissue in the vacuum cavity.

In another embodiment, a system comprises a medical device and an implantable medical elongated member configured to deliver a therapy from the medical device to a target therapy delivery site in a patient. The elongated member comprises an elongated body extending between a proximal end configured to couple to the medical device and a distal end. The elongated body defines a vacuum cavity configured to receive vacuum pressure from a vacuum source to draw tissue of the patient into the vacuum cavity. The implantable elongated member further comprises a channel disposed within the elongated body and a fixation element disposed within the channel and configured to engage with the tissue in the vacuum cavity.

In another embodiment, a method comprises inserting an implantable medical elongated member into a patient, the implantable medical elongated member comprising an elongated body extending between a proximal end configured to couple to a medical device and a distal end, a vacuum cavity defined by the elongated body and configured to receive tissue of the patient, a channel disposed within the elongated body, and a fixation element disposed within the channel.

The method further comprises advancing the implantable medical elongated member to a target therapy delivery site within the patient, applying negative pressure to the vacuum cavity of the implantable medical elongated member to draw tissue adjacent to the vacuum cavity into the vacuum cavity, and drawing the fixation element of implantable medical elongated member into engagement with the tissue in the vacuum cavity to fix the implantable medical elongated member to the target therapy delivery site.

The details of one or more embodiments are set forth in the accompanying drawings and the description below. Other features, objects, and advantages will be apparent from the description and drawings, and from the claims.

DETAILED DESCRIPTION

This disclosure describes techniques for securing an implantable medical elongated member, such as a medical lead or a catheter, to tissue within a patient. The elongated member is configured to be coupled to a medical device to deliver a therapy from the medical device to target therapy delivery site in a patient. The fixation techniques of this disclosure secure the elongated member to the tissue of the patient to prevent the elongated member from migrating away from the target therapy delivery site, which may adversely affect the therapy. For example, migration of a medical lead from the target therapy delivery site may cause one or more electrodes of the lead to migrate from the target tissue location, resulting in reduction in therapy efficacy.

In accordance with the invention, the implantable medical elongated member is substantially fixed to surrounding tissue by applying suction from a vacuum to a vacuum cavity defined by the elongated member to draw tissue adjacent to the vacuum cavity into the vacuum cavity. The elongated member includes a fixation element that engages with the captured tissue within the vacuum cavity to substantially fix a position of the elongated member with respect to the target therapy delivery site. As an example, a pin may be driven through the tissue within the vacuum cavity to fix the elongated member to the target therapy delivery site.

Various embodiments of the elongated member may be applicable to different therapeutic applications. For example, the elongated member may be a medical lead that is used to deliver electrical stimulation to a target stimulation site, such as one or more nerves or muscles of a patient. In another embodiment, the elongated member may be a catheter that is placed to deliver a fluid, such as pharmaceutical agents, insulin, pain relieving agents, gene therapy agents, or the like from a fluid reservoir and/or pump to a target tissue site in a patient. The techniques of this disclosure are applicable to any configuration or type of implantable elongated member that is used to deliver therapy to a site in a patient. For purposes of illustration, however, the disclosure will refer to a medical lead for delivering electrical stimulation therapy.

Figure 1:
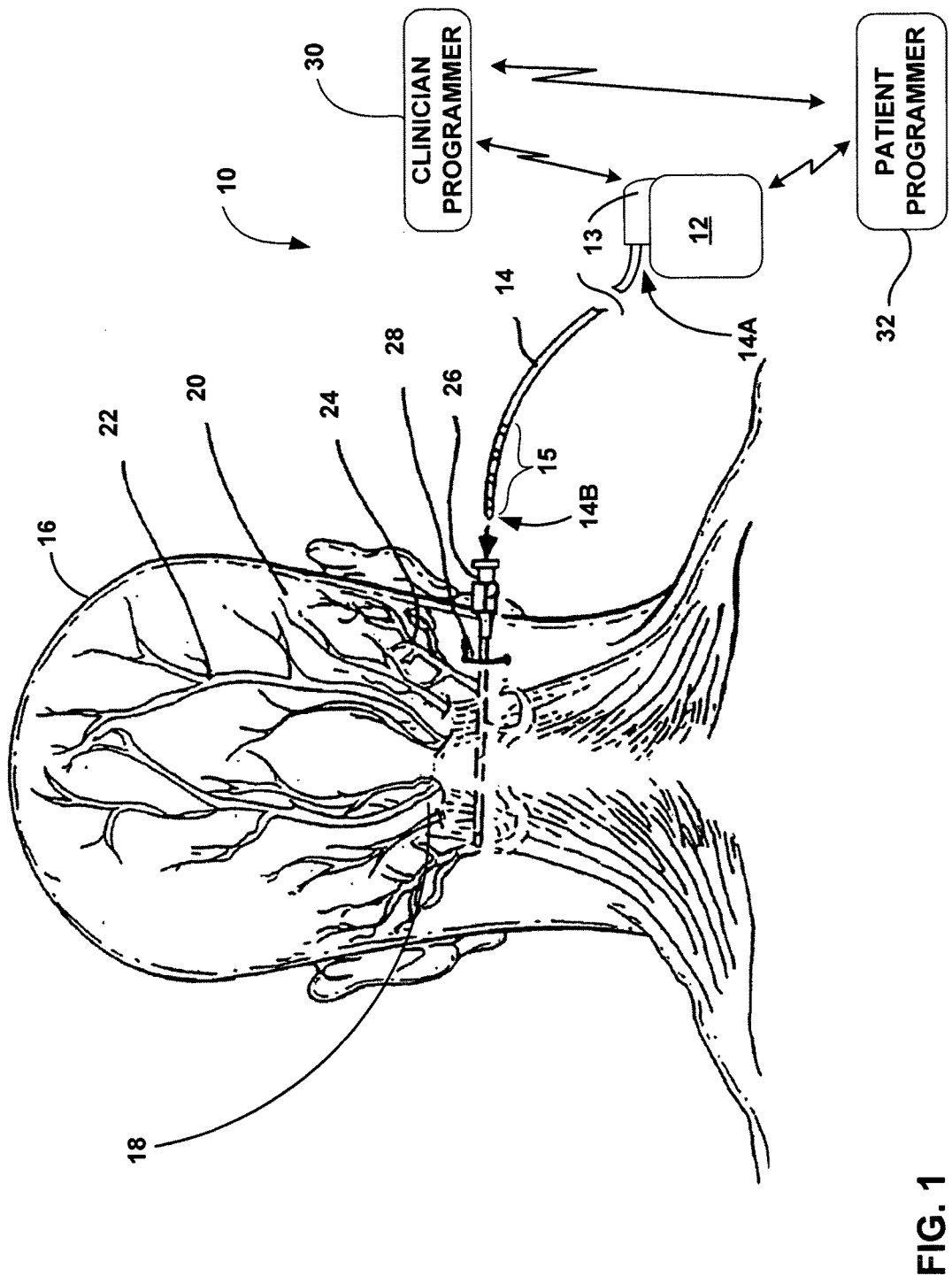
FIG. 1 is a schematic perspective view of a therapy system that includes an electrical stimulator coupled to a stimulation lead.

FIG. 1 is a schematic perspective view of a therapy system 10, which includes an electrical stimulator coupled to a stimulation lead. In the example illustrated in FIG. 1, the electronic stimulator comprises a neurostimulator 12 and the lead comprises a neurostimulation lead 14. Neurostimulator 12, may be either implantable or external. For example, neurostimulator 12 may be subcutaneously implanted in the body of a patient 16 (e.g., in a chest cavity, lower back, lower abdomen, or buttocks of patient 16). Neurostimulator 12 provides a programmable stimulation signal (e.g., in the form of electrical pulses or substantially continuous-time signals) that is delivered to a target stimulation site 18 within patient 16 by neurostimulation lead 14, and more particularly, via one or more stimulation electrodes 15 carried by lead 14. Neurostimulator 12 may also be referred to as a pulse or signal generator. In some embodiments, lead 14 may also carry one or more sense electrodes (not shown in FIG. 1) to permit neurostimulator 12 to sense electrical signals from target stimulation site 18. Furthermore, in some embodiments, neurostimulator 12 may be coupled to two or more leads, e.g., for bilateral or multi-lateral stimulation.

A proximal end 14A of lead 14 may be both electrically and mechanically coupled to a connector 13 of neurostimulator 12 either directly or indirectly (e.g., via a lead extension). In particular, conductors disposed in the lead body may electrically connect stimulation electrodes 15 (and sense electrodes, if present) adjacent to a distal end 14B of lead 14 to neurostimulator 12.

In the embodiment of therapy system 10 shown in FIG. 1, target stimulation site 18 is proximate to an occipital region of a patient 16. As described in greater detail below, lead 14 further includes a fixation mechanism (not shown in FIG. 1) to fixate lead 14 to target stimulation site 18. In particular, lead 14 may be implanted and fixated with the fixation mechanism proximate to the occipital region of patient 16 for stimulation of one or more occipital nerves. In particular, lead 14 may be implanted proximate to lesser occipital nerve 20, greater occipital nerve 22, and third occipital nerve 24. In FIG. 1, lead 14 is aligned to be introduced into a lead placement device, such as introducer needle 26, and implanted and anchored or fixated with one or more fixation elements proximate to target stimulation site 18 in the occipital region of patient 16 for stimulation of one or more occipital nerves 20, 22, and/or 24. In particular, neurostimulator 12 may deliver stimulation therapy to any one or more of lesser occipital nerve 20, greater occipital nerve 22 or third occipital nerve 24 via electrodes 15 disposed adjacent to distal end 14B of lead 14. In alternate embodiments, lead 14 may be positioned proximate to one or more other peripheral nerves proximate to occipital nerves 20, 22, and 24 of patient 16, such as nerves branching from occipital nerves 20, 22, and 24, as well as stimulation of any other suitable nerves, organs, muscles or muscle groups throughout patient 16, such as, but not limited to, nerves within a brain, stomach or spinal cord of patient 16.

Implantation of lead 14 may involve the subcutaneous placement of lead 14 transversely across one or more occipital nerves 20, 22, and/or 24 that are causing patient 16 to experience pain. In one example method of implanting lead 14 proximate to the occipital nerve, using local anesthesia, a vertical skin incision 28 approximately two centimeters in length is made in the neck of patient 16 lateral to the midline of the spine at the level of the C1 vertebra. The length of vertical skin incision 28 may vary depending on the particular patient. At this location, the skin and muscle of patient 16 are separated by a band of connective tissue referred to as fascia. Introducer needle 26 is introduced into the subcutaneous tissue, superficial to the fascia and muscle layer but below the skin. Occipital nerves 20, 22, and 24 are located within the cervical musculature and overlying fascia, and as a result, introducer needle 26 and, eventually, lead 14 are inserted superior to occipital nerves 20, 22, and 24.

Once introducer needle 26 is fully inserted, lead 14 may be advanced through introducer needle 26 and positioned to allow stimulation of the lesser occipital nerve 20, greater occipital nerve 22, third occipital nerve 24, and/or other peripheral nerves proximate to any of the occipital nerves 20, 22, and 24. Once positioned, lead 14 is fixated to target stimulation site 18 using one or more fixation mechanisms. As described in greater detail below, lead 14 includes a vacuum channel that applies a negative pressure in at least one vacuum cavity (not shown in FIG. 1) to capture in a portion of tissue from occipital region 18 into the vacuum cavity. Lead 14 is fixed to the tissue drawn into the vacuum cavity using a fixation element, such as a pin or screw. Upon fixing of lead 14 to target stimulation site 18, introducer needle 26 may be removed. Lead 14 may include one or more vacuum cavities along any portion of lead 14. For example, in some embodiments, lead 14 may include one or more vacuum channels and fixation elements at an intermediate portion of lead 14 (i.e., at a portion between proximal end 14A and distal end 14B) and/or at a proximal portion of lead 14 near proximal end 14A in order to substantially fix lead 14 at its intermediate portion and/or proximal portion.

Accurate lead placement may affect the success of occipital nerve stimulation. If lead 14 is located too deep, i.e., anterior, in the subcutaneous tissue, patient 16 may experience muscle contractions, grabbing sensations, or burning. Such problems may additionally occur if lead 14 migrates after implantation. Furthermore, due to the location of implanted lead 14 on the back of the neck of patient 16, lead 14 may be subjected to pulling and stretching that may increase the chances of lead migration. For these reasons, fixating lead 14 may be advantageous.

Therapy system 10 also may include a clinician programmer 30 and a patient programmer 32. Clinician programmer 30 may be a handheld computing device that permits a clinician to program neurostimulation therapy for patient 16, e.g., using input keys and a display. For example, using clinician programmer 30, the clinician may specify neurostimulation parameters for use in delivery of neurostimulation therapy. Clinician programmer 30 supports telemetry (e.g., radio frequency telemetry) with neurostimulator 12 to download neurostimulation parameters and, optionally, upload operational or physiological data stored by neurostimulator 12. In this manner, the clinician may periodically interrogate neurostimulator 12 to evaluate efficacy and, if necessary, modify the stimulation parameters.

Like clinician programmer 30, patient programmer 32 may be a handheld computing device. Patient programmer 32 may also include a display and input keys to allow patient 16 to interact with patient programmer 32 and neurostimulator 12. In this manner, patient programmer 32 provides patient 16 with an interface for control of neurostimulation therapy by neurostimulator 12. For example, patient 16 may use patient programmer 32 to start, stop or adjust neurostimulation therapy. In particular, patient programmer 32 may permit patient 16 to adjust stimulation parameters such as duration, amplitude, pulse width and pulse rate, within an adjustment range specified by the clinician via clinician programmer 32, or select from a library of stored stimulation therapy programs.

Neurostimulator 12, clinician programmer 30, and patient programmer 32 may communicate via cables or a wireless communication, as shown in FIG. 1. Clinician programmer 30 and patient programmer 32 may, for example, communicate via wireless communication with neurostimulator 12 using RF telemetry techniques known in the art. Clinician programmer 30 and patient programmer 32 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Figure 4:
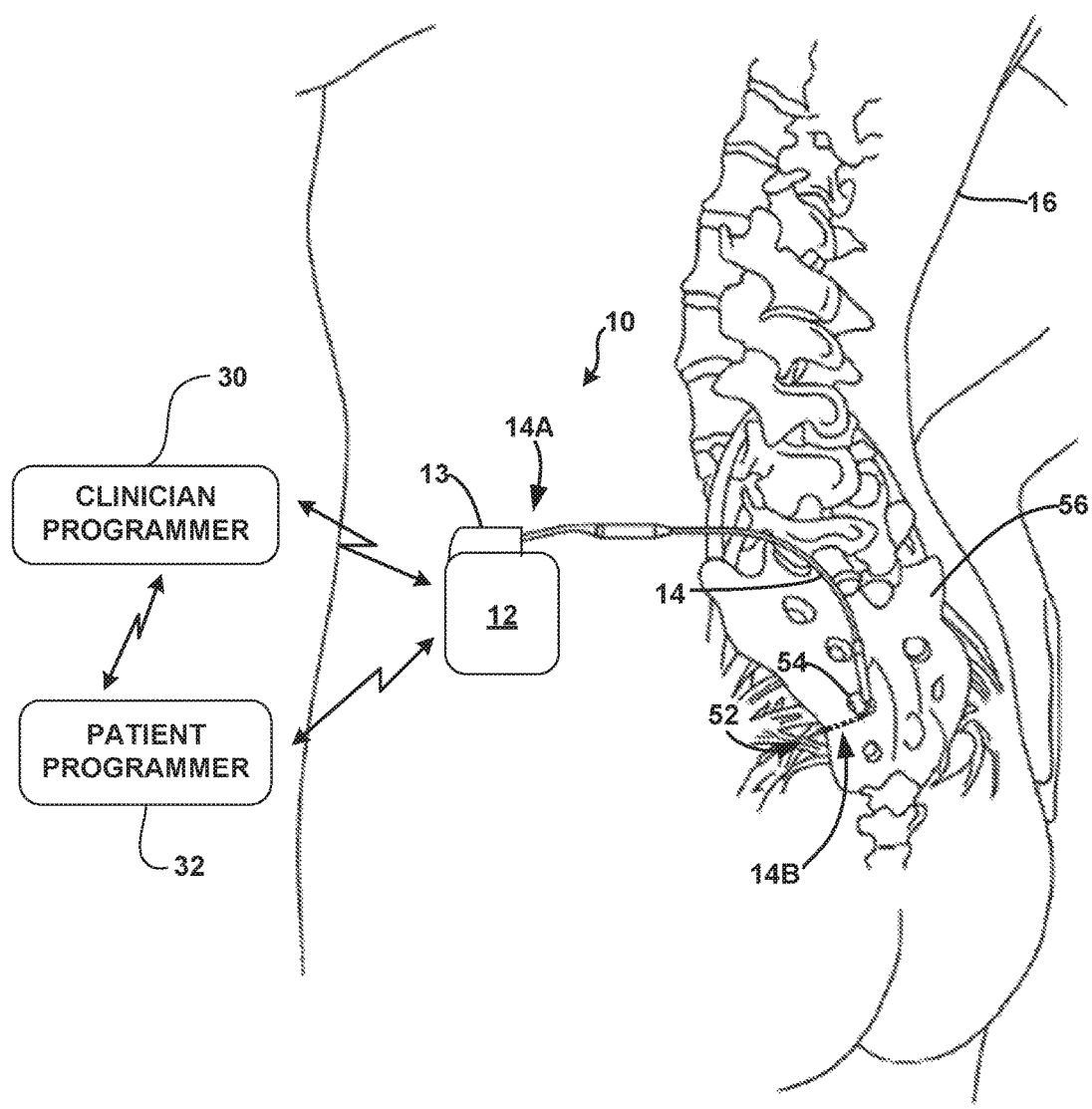
FIG. 4 is a block diagram illustrating a therapy system implanted within a different location of a patient.

Therapy system 10 may also be used to provide stimulation therapy to other nerves of patient 16. In alternate applications of lead 14, therapy system 10 may be used to provide stimulation therapy proximate to one or more sacral nerves in patient 16, an example of which is shown in FIG. 4, or any other suitable nerve, organ, muscle, muscle group or another target tissue site in patient 16, which may be selected based on, for example, a therapy program selected for a particular patient. For example, therapy system 10 may be used to deliver neurostimulation therapy to a pudendal nerve, a perineal nerve or other areas of the nervous system, in which cases, lead 14 would be implanted and substantially fixed proximate to the respective nerve. As further examples, lead 14 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. Accordingly, although patient 16 and target stimulation site 18 of FIG. 1 are referenced throughout the remainder of the disclosure for purposes of illustration, a neurostimulation lead 14 in accordance with this disclosure may be adapted for use in a variety of electrical stimulation applications.

Figure 2:
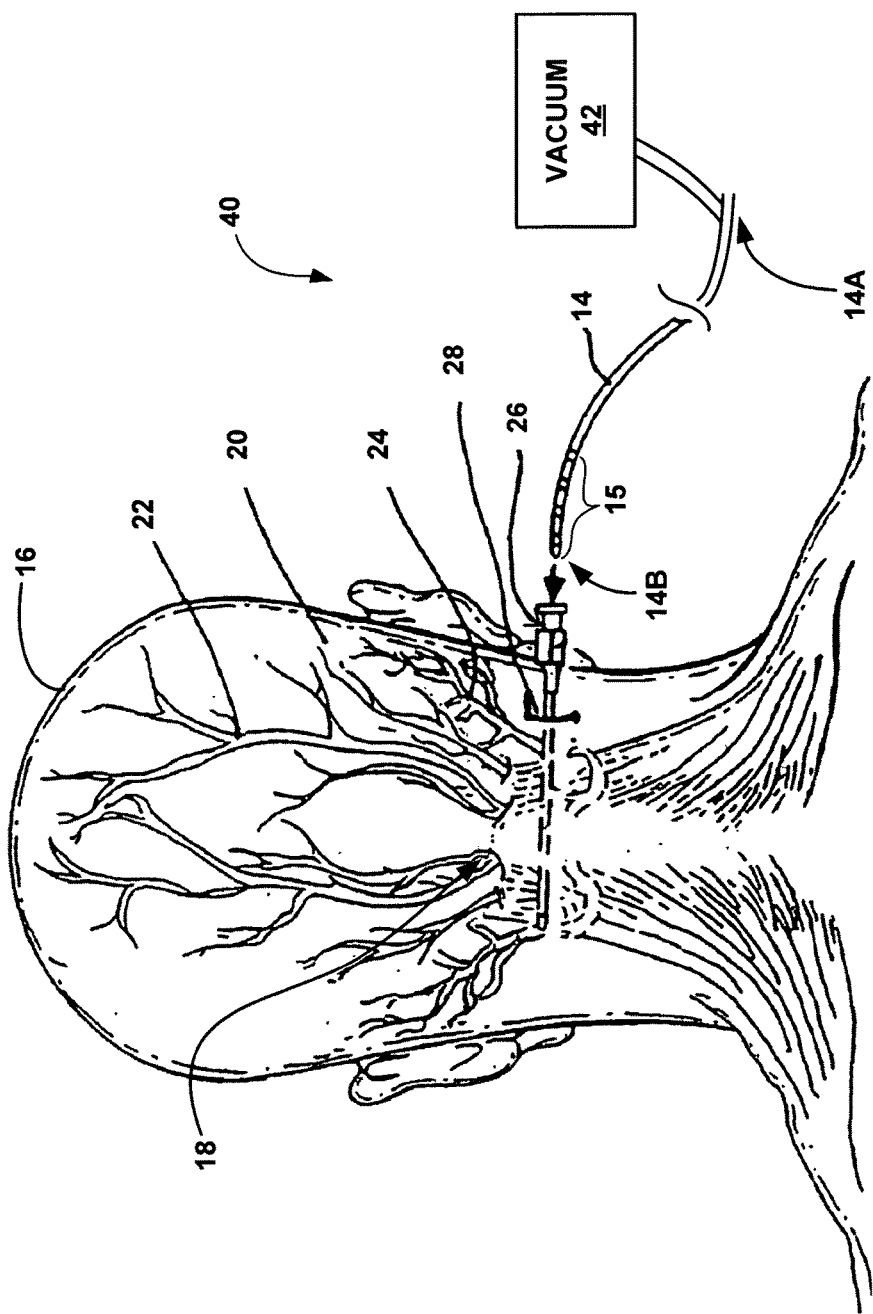
FIG. 2 is a schematic perspective view of an exemplary lead placement system for placing a lead at a target stimulation site of a patient.

FIG. 2 is a schematic perspective view of a lead placement system 40 for placing lead 14 at a target stimulation site 18 of patient 16. As described above, lead 14 may be implanted such that electrodes 15 are implanted and fixed proximate to lesser occipital nerve 20, greater occipital nerve 22, and third occipital nerve 24. As illustrated in FIG. 2, lead 14 is aligned to be introduced into a lead placement device, such as introducer needle 26, in order to be implanted proximate to an occipital region of patient 16.

As discussed above in reference to FIG. 1, in one embodiment of implanting lead 14 proximate to the occipital region of patient 16, introducer needle 26 is introduced into the subcutaneous tissue within the neck of patient 16 via vertical skin incision 28, superficial to the fascia and muscle layer but below the skin. Introducer needle 26 is positioned such that it is superior to occipital nerves 20, 22 and 24. Once introducer needle 26 is fully inserted, lead 14 may be advanced through introducer needle 26 and positioned to allow stimulation via electrodes 15 of the lesser occipital nerve 20, greater occipital nerve 22, third occipital nerve 24, and/or other peripheral nerves proximate to any of the occipital nerves. Once positioned electrodes 15 are positioned in operative relation to target stimulation site 18, introducer needle 26 is slightly retracted (toward proximal end of lead 14B) to expose distal end 14A of lead 14 to target stimulation site 18. At this point, one or more trial stimulations may be performed to ensure that lead 14 is placed in the correct location within target stimulation site 18.

Upon verification that electrodes 15 of lead 14 are properly placed for stimulation of target stimulation site 18, lead 14 is fixated to target stimulation site 18. In particular, lead 14 includes a fixation mechanism that includes a vacuum chamber to receive adjacent tissue and a fixation mechanism to fix lead 14 to the received tissue. As FIG. 2 schematically illustrates, lead 14 includes a vacuum channel (not shown in FIG. 2) that is coupled to a vacuum 42. In the embodiment shown in FIG. 2, the vacuum channel extends from proximal end 14A of lead 14 to at least one vacuum cavity (not shown in FIG. 2) proximate to distal end 14B of lead 14. The vacuum cavity may be at distal end 14B of lead 14, proximate to distal end 14B, between electrodes 15, and/or between electrodes 15 and proximal end 14A of lead 14. In another embodiment, lead 14 may define vacuum cavities at one or more intermediate locations between proximal end 14A and distal end 14B of lead 14, as well as proximate to proximal end 14A of lead 14. The vacuum channel and vacuum cavity are in fluidic communication. Vacuum 42 applies suction (i.e., a negative pressure) within the vacuum channel to draw tissue, such as tissue proximate to target stimulation site 18, into the vacuum cavity.

A fixation element (not shown in FIG. 2) that is at least partially disposed within lead 14 fixes distal end 14B of lead 14 to the tissue that is drawn into the vacuum cavity by the suction force applied by vacuum 42. As an example, in one embodiment, a fastening pin is driven into the tissue drawn into the vacuum cavity to fix distal end 14B of lead 14 proximate to target stimulation site 18. After fixing lead 14 to target stimulation site 18, introducer needle 26 may be withdrawn from patient 16. Lead 14 may then be coupled to neurostimulator 12 (FIG. 1), which may deliver stimulation therapy to any one or more of lesser occipital nerve 20, greater occipital nerve 22 or third occipital nerve 24 via electrodes 15 disposed adjacent to distal end 14B of lead 14.

Figure 3:
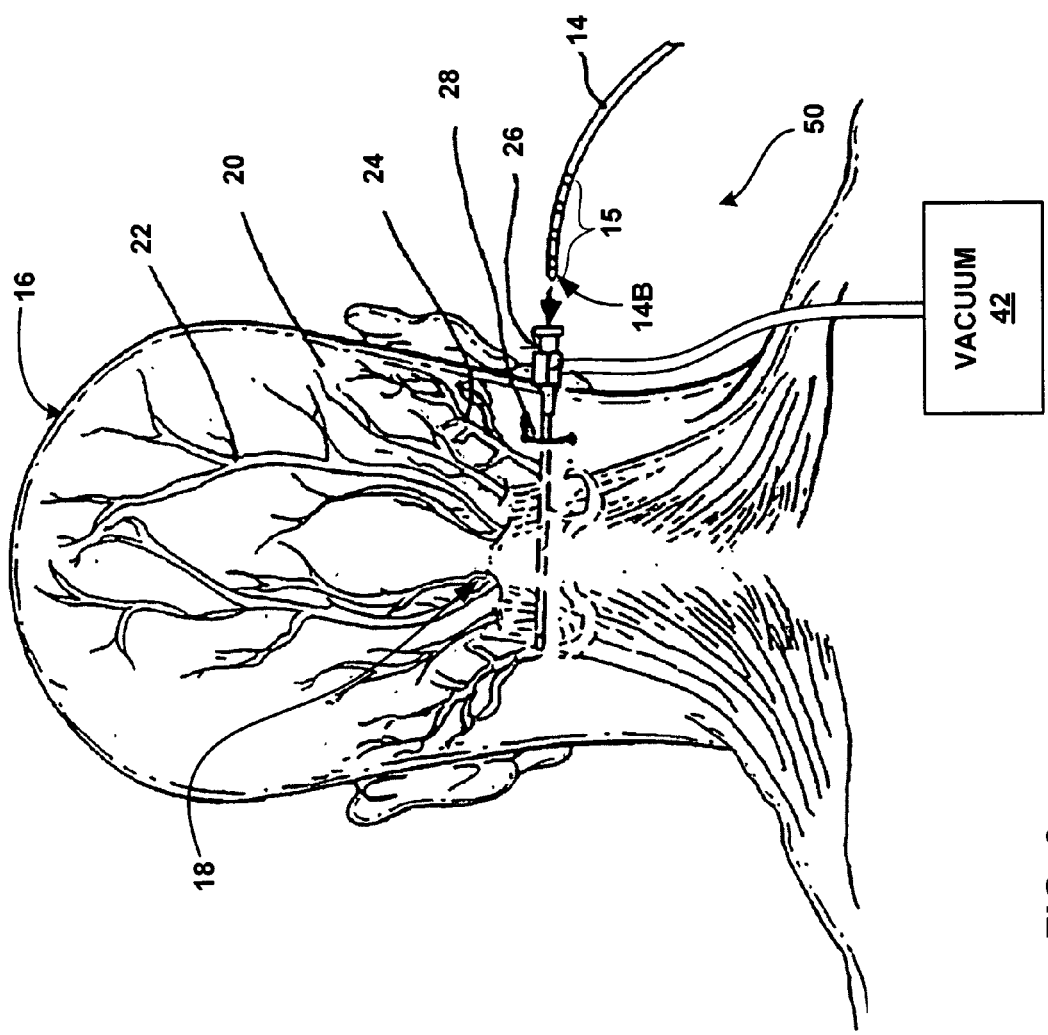
FIG. 3 is a schematic perspective view of another exemplary lead placement system for placing a lead at a target stimulation site of a patient.

FIG. 3 is a schematic perspective view of another embodiment of lead placement system 50 for placing lead 14 at a target stimulation site 18 of patient 16. Lead placement system 50 substantially conforms to lead placement system 40 of FIG. 2, but lead placement system 50 includes a vacuum channel (not shown in FIG. 3) within introducer needle 28 instead of within lead 14.

In particular, introducer needle 28 includes a vacuum channel that couples to vacuum 42. The vacuum channel extends the length of introducer needle 28, and is in fluidic communication with at least one vacuum cavity (not shown in FIG. 3) proximate to distal end 14B of lead 14. Thus, the vacuum channel within introducer needle 26 couples vacuum 42 to the vacuum cavity within lead 14. As described above, in another embodiment, lead 14 may include one or more vacuum cavities at one or more intermediate locations between proximal end 14A and distal end 14B of lead 14 and/or proximate to proximal end 14A of lead 14. As described above, vacuum 42 applies suction (i.e., a negative pressure) within the vacuum channel to draw tissue adjacent to the vacuum cavity (e.g., at target stimulation site 18 where the vacuum cavity is proximate to target stimulation site 18) into the vacuum cavity proximate to distal end 14B of lead 14, and a fixation element fixates the distal end of lead 14 to the portion of the tissue drawn into the vacuum cavity.

FIG. 4 is a block diagram illustrating therapy system 10 implanted within a different location of a patient 16. In the embodiment of therapy system 10 shown in FIG. 4, target stimulation site 52 is proximate to the S3 sacral nerve of patient, and lead 14 has been introduced into the S3 sacral foramen 54 of sacrum 56 to access the S3 sacral nerve. Stimulation of the S3 sacral nerve may help treat pelvic floor disorders, urinary control disorders, fecal control disorders, interstitial cystitis, sexual dysfunction, and pelvic pain.

Therapy system 10 and, more particularly, lead 14 of therapy system 10 may be implanted and fixated within patient 16 in accordance with the techniques of this disclosure. In one embodiment, a lead introducer (not illustrated in FIG. 4) is inserted into the S3 sacral foramen 54 of sacrum 56 to access the S3 sacral nerve. Lead 14 is advanced through the lead introducer and positioned to allow stimulation of the target stimulation site 52. Once positioned, lead 14 is fixated to surrounding tissue by applying suction to at least one vacuum cavity (not shown in FIG. 1) to draw a portion of tissue into the vacuum cavity and engaging a fixation element with the tissue drawn into the vacuum cavity.

As described above, therapy system 10 is useful in electrical stimulation applications other than an occipital nerve stimulation application (FIG. 1) and a sacral nerve stimulation application (FIG. 4). Thus, in alternate embodiments, target stimulation site 18 or 54 may be a location proximate to any of the other sacral nerves in patient 16 or any other suitable nerve, organ, muscle, muscle group or another tissue site in patient 16, which may be selected based on, for example, a therapy program selected for a particular patient.

Figure 5:
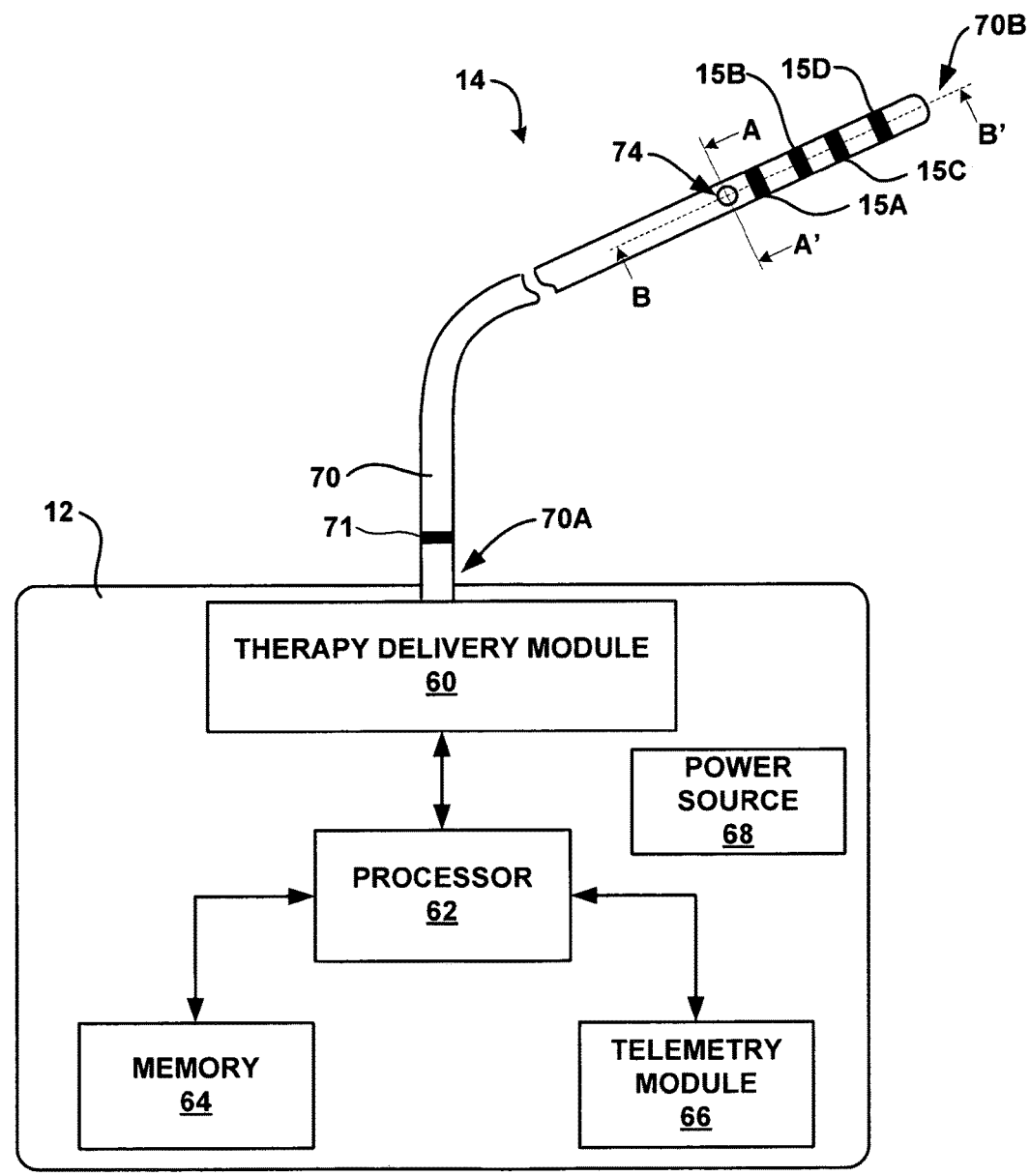
FIG. 5 is a block diagram illustrating various components of neurostimulator and an implantable lead.

FIG. 5 is a block diagram illustrating various components of neurostimulator 12 and an implantable lead 14. Neurostimulator 12 includes therapy delivery module 60, processor 62, memory 64, telemetry module 66, and power source 68. In some embodiments, neurostimulator 12 may also include a sensing circuit (not shown in FIG. 5). Implantable lead 14 includes elongated lead body 70 extending between proximal end 70A and distal end 70B. Lead body 70 may be a cylindrical or may be a paddle-shaped (i.e., a "paddle" lead). Implantable lead 14 also includes electrodes 15A-15D (collectively "electrodes 15") disposed on lead body 70 adjacent to distal end 70B of lead body 70. The configuration, type, and number of electrodes 15 illustrated in FIG. 5 are merely exemplary.

In some embodiments, electrodes 15 may be ring electrodes. In other embodiments, electrodes 15 may be segmented or partial ring electrodes, each of which extends along an arc less than 360 degrees (e.g., 60-120 degrees) around the periphery of lead body 70. In embodiments in which lead 14 is a paddle lead, electrodes 15 may extend along one side of lead body 70. Electrodes 15 extending around a portion of the circumference of lead body 70 or along one side of a paddle lead may be useful for providing an electrical stimulation field in a particular direction/targeting a particular therapy delivery site. For example, in the electrical stimulation application shown in FIG. 1, electrodes 15 may be disposed along lead body 70 such that the electrodes 15 face toward occipital nerves 20, 22, and/or 24, or otherwise away from the scalp of patient 16. This may be an efficient use of stimulation energy because electrical stimulation of the scalp may not provide any useful therapy or minimally useful therapy to patient 16. In addition, the use of segmented or partial ring electrodes 15 may also reduce the overall power delivered to electrodes 15 by neurostimulator 12 because of the efficient delivery of stimulation to occipital nerves 20, 22, and/or 24 (or another target stimulation site) by eliminating or minimizing the delivery of stimulation to unwanted or unnecessary regions within patient 16.

In embodiments in which electrodes 15 extend around a portion of the circumference of lead body 70 or along one side of a paddle lead, lead 14 may include one or more orientation markers 71 proximate to proximal end 14A that indicate the relative location of electrodes 15. Orientation marker 71 may be a printed marking on lead body 70, an indentation in lead body 70, a radiographic marker, or another type of marker that is visible or otherwise detectable (e.g., detectable by a radiographic device) by a clinician. Orientation marker 71 may help a clinician properly orient lead 14 such that electrodes 15 face the desired direction (e.g., toward occipital nerves 20, 22, and/or 24) within patient 16. For example, orientation marker 71 may also extend around the same portion of the circumference of lead body 70 or along the side of the paddle lead as electrodes 15. In this way, orientation marker 71 faces the same direction as electrodes, thus indicating the orientation of electrodes 15 to the clinician. When the clinician implants lead 14 in patient 16, orientation marker 71 may remain visible to the clinician.

Neurostimulator 12 delivers stimulation therapy via electrodes 15 of lead 14. In particular, electrodes 15 are electrically coupled to a therapy delivery module 60 of neurostimulator 12 via conductors within lead body 70. In one embodiment, an implantable signal generator or other stimulation circuitry within therapy delivery module 60 delivers electrical signals (e.g., pulses or substantially continuous-time signals, such as sinusoidal signals) to targets stimulation site 18 (FIG. 1A) via at least some of electrodes 15 under the control of a processor 62. The implantable signal generator may be coupled to power source 68. Power source 68 may take the form of a small, rechargeable or non-rechargeable battery, or an inductive power interface that transcutaneously receives inductively coupled energy. In the case of a rechargeable battery, power source 68 similarly may include an inductive power interface for transcutaneous transfer of recharge power.

The stimulation energy generated by therapy delivery module 60 may be formulated as neurostimulation energy, e.g., for treatment of any of a variety of neurological disorders, or disorders influenced by patient neurological response. The signals may be delivered from therapy delivery module 60 to electrodes 15 via a switch matrix and conductors carried by lead 14 and electrically coupled to respective electrodes 15.

Processor 62 may include a microprocessor, a controller, a DSP, an ASIC, an FPGA, discrete logic circuitry, or the like. Processor 62 controls the implantable signal generator within therapy delivery module 60 to deliver neurostimulation therapy according to selected stimulation parameters. Specifically, processor 62 controls therapy delivery module 60 to deliver electrical signals with selected amplitudes, pulse widths (if applicable), and rates specified by the programs. In addition, processor 62 may also control therapy delivery module 60 to deliver the neurostimulation signals via selected subsets of electrodes 15 with selected polarities. For example, electrodes 15 may be combined in various bipolar or multi-polar combinations to deliver stimulation energy to selected sites, such as nerve sites adjacent the spinal column, pelvic floor nerve sites, or cranial nerve sites.

Processor 62 may also control therapy delivery module 60 to deliver each signal according to a different program, thereby interleaving programs to simultaneously treat different symptoms or provide a combined therapeutic effect. For example, in addition to treatment of one symptom such as sexual dysfunction, neurostimulator 12 may be configured to deliver neurostimulation therapy to treat other symptoms such as pain or incontinence.

Memory 64 of neurostimulator 12 may include any volatile or non-volatile media, such as a RAM, ROM, NVRAM, EEPROM, flash memory, and the like. In some embodiments, memory 64 of neurostimulator 12 may store multiple sets of stimulation parameters that are available to be selected by patient 16 via patient programmer 32 (FIG. 1) or a clinician via clinician programmer 30 (FIG. 1) for delivery of neurostimulation therapy. For example, memory 64 may store stimulation parameters transmitted by clinician programmer 30 (FIG. 1). Memory 64 also stores program instructions that, when executed by processor 62, cause neurostimulator 12 to deliver neurostimulation therapy. Accordingly, computer-readable media storing instructions may be provided to cause processor 62 to provide functionality as described herein.

In particular, processor 62 controls telemetry module 66 to exchange information with an external programmer, such as clinician programmer 30 and/or patient programmer 32 (FIG. 1), by wireless telemetry. In addition, in some embodiments, telemetry module 66 supports wireless communication with one or more wireless sensors that sense physiological signals and transmit the signals to neurostimulator 12.

Migration of lead 14 following implantation may be undesirable, and may have detrimental effects on the quality of therapy delivered to a patient 16. For example, with respect to the occipital nerve stimulation application shown in FIG. 1 or the sacral nerve stimulation application shown in FIG. 4, migration of lead 14 may cause displacement of electrodes carried by lead 14 to a target stimulation site 18 or 52. As a result, the electrodes may not be properly positioned to deliver the therapy to target stimulation site 18 or 52, resulting in reduced electrical coupling, and possibly undermining therapeutic efficacy of the neurostimulation therapy from system 10. Substantially fixing lead 14 to surrounding tissue may help prevent lead 14 from migrating from target stimulation site 18 or 52 following implantation, which may ultimately help avoid harmful effects that may result from a migrating neurostimulation lead 14.

To that end, lead 14 further includes a fixation mechanism including vacuum cavity 74 and a fixation element located proximate to electrodes 15 on lead body 70. Lead body 70 may define vacuum cavity 74. As described above, suction is applied to vacuum cavity 74 via vacuum source 42 (FIGS. 2 and 3) to draw tissue surrounding lead 14 into vacuum cavity 74. The fixation element is coupled to the tissue drawn into vacuum cavity 74 to fixate lead 14 to tissue surrounding lead 14, such as tissue at the occipital region in the example of FIG. 1 or tissue within sacrum 56 in the example of FIG. 4. In this way, vacuum cavity 74 may also be referred to as a tissue receiving fixation cavity.

While in the embodiment shown in FIG. 5, lead 14 includes a single vacuum cavity 74 located proximate to electrodes 15, in other embodiments, a lead may include any suitable number of vacuum cavities in any suitable arrangement with respect to electrodes 15. For example, in one embodiment, vacuum cavity 74 may be located distal to electrodes 15 on lead body 70 or between individual electrodes 15A-15D. Moreover, lead 14 may include a plurality of vacuum cavities at locations distal to electrodes 15, between individual electrodes 15A-15D, and/or proximate to electrodes 15 in order to substantially fix electrodes 15 proximate to target stimulation site 18. Examples of these embodiments are shown in FIGS. 9A-9E.

In addition, as described above, in some embodiments, lead 14 may include one or more vacuum cavities proximate to proximal end 70A of lead body 70 or at an intermediate location (e.g., midway) between proximal end 70A and distal end 70A of lead body 70. For example, as described in commonly-assigned U.S. patent application Ser. No. 11/591,448 by Martin T. Gerber, entitled "IMPLANTABLE MEDICAL ELONGATED MEMBER INCLUDING AN INTERMEDIATE FIXATION ELEMENT", filed on the same date as the present disclosure and issued as U.S. Pat. No. 9,713,706 on Jul. 25, 2017, and incorporated herein by reference in its entirety, lead body 70 may define three substantially equal-sized portions, a proximal portion, distal portion, and middle portion, which is located between the proximal and distal portions. In accordance with embodiments of the present invention, lead body 70 may include vacuum cavities and fixation elements at the proximal portion, distal portion, and/or middle portion in order to fix lead body 70 at points along the proximal portion, distal portion, and/or middle portion. Intermediate fixation of lead 14 may be useful in applications in which distal end 14A of lead 14 is implanted a relatively long distance from neurostimulator 12 and/or if lead 14 is implanted in a region of patient 16 that undergoes a relatively large range of motion or relatively frequent movement (e.g., a back or joint).

In one embodiment, vacuum cavity 74 may be approximately sized to draw in enough tissue to substantially fix lead 14. As an example, in a neurostimulation lead with approximately a 1 millimeter (mm) diameter, vacuum cavity 74 may have an approximate cross-sectional depth D (measured in a radial direction) of approximately 0.25 mm and an approximate cross-sectional width W of approximately 0.25 mm. In some embodiments, vacuum cavity 74 may have a depth D and width W of about 10 percent (%) to about 50% the diameter of lead body 70. Depth D and width W need not be the same value. Although vacuum cavity 74 illustrated in FIG. 5 is illustrated as a circle, vacuum cavity 74 may take other shapes, such as an oval. Additionally, vacuum cavity 74 may simply comprise a slot.

In comparison to some existing methods of fixing implanted medical leads, such as suturing lead 14 to surrounding tissue, fixing implanted medical leads by suctioning tissue into vacuum cavity 74 and engaging a fixation element with the tissue to fix the lead to the tissue within the cavity 74 may permit implantation of lead 14 in patient 16 via a minimally invasive surgery, which may allow for reduced pain and discomfort for patient 16 relative to surgery, as well as a quicker recovery time. Moreover, the fixation techniques of this disclosure further permit fixation of lead 14 to target stimulation site 18 anywhere along lead 14. Some other techniques may only permit distal fixation of a lead to the target stimulation site, which may cause nerve damage.

Figure 6:
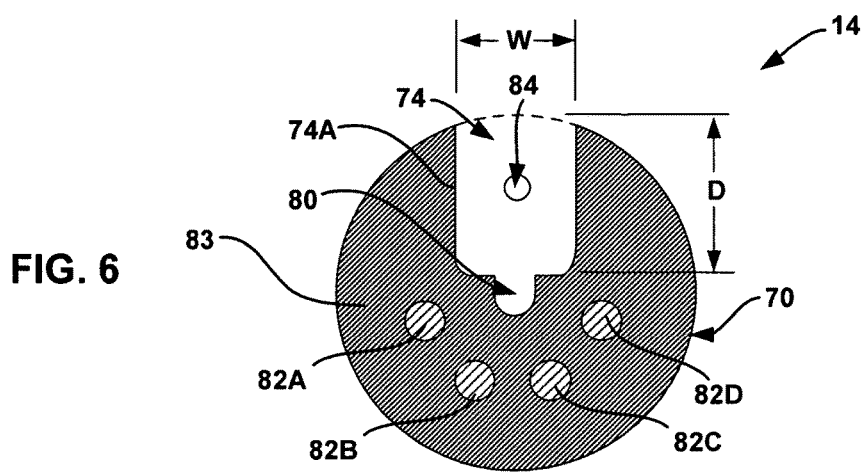
FIG. 6 is a schematic diagram illustrating a cross-sectional view of the lead taken along line A to A' in FIG. 5.

FIG. 6 illustrates a schematic cross-sectional view of lead 14 taken along line A to A' in FIG. 5. As previously discussed, lead body 70 of lead 14 defines a vacuum cavity 74 into which tissue from target stimulation site 18 (FIG. 1) is drawn via the suction applied from vacuum 42 (FIG. 2). Lead 14 also includes a vacuum channel 80 that is in fluidic communication with vacuum cavity 74. As described above, vacuum channel 80 extends from proximal end 14A of lead 14 to vacuum cavity 74. At its proximal end, vacuum channel 80 couples to vacuum 42. Vacuum 42 applies suction to vacuum cavity 74 via vacuum channel 80 to draw tissue adjacent to vacuum cavity 74 into vacuum cavity 74.

Lead 14 also includes an opening 84 through which a fixation element, such as a fixation pin or screw, enters vacuum cavity 74 to engage with the tissue drawn into vacuum cavity 74 and thereby attach lead 14 to the tissue. As an example, a fastening screw may be driven into the tissue drawn into vacuum cavity 74 to fix distal end of lead 14 to target stimulation site 18.

Lead 14 also includes conductors 82A-82D (collectively "conductors 82") that are disposed within lead body 70 and electrically connect stimulation electrodes 15A-D, respectively, (and sense electrodes, if present) to neurostimulator 12 (FIG. 1). In the embodiment shown in FIG. 6, a distal end of each of conductors 82 is electrically coupled to a respective one of electrodes 15 and a proximal end of each of conductors 82 terminates at an electrical contact disposed at proximal end 70A of lead body 70. The electrical contacts may then electrically connect to a lead extension or directly to neurostimulator 12. Separate conductors for each of electrodes 15 enables neurostimulator 12 to independently select individual electrodes 15 for delivering the stimulation therapy to target therapy delivery site 18. In other embodiments, a lead may include a fewer or greater number of conductors 82. For example, a lead may include only two conductors and each of the conductors may electrically couple a pair of electrodes to neurostimulator 12. In this manner, there may not be a one-to-one correspondence between conductors 82 and electrodes 15.

Electrically conductive conductors 82 are electrically insulated from each other by insulating layer 83, which also surrounds conductors 82 in order to electrically insulate conductors 82 from tissue when lead 14 is implanted in patient 16 and from a clinician when the clinician is implanting lead 14 in a patient. In the embodiment of FIG. 6, vacuum cavity 74 is formed in insulating layer 83 using any suitable method. For example, insulating layer 83 may be molded, embossed, etched, cut or milled to define vacuum cavity 74. Another material may also line wall 74A of vacuum cavity 74 to provide support for walls 74A.

Figure 7A:
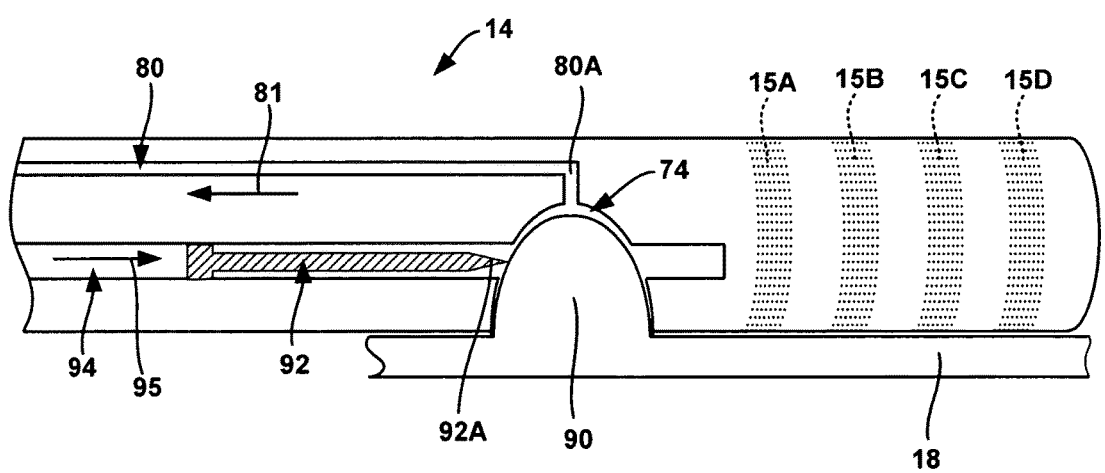
FIGS. 7A and 7B are schematic diagrams illustrating cross-sectional side views of a lead taken along line B to B' in FIG. 5.
Figure 7B:
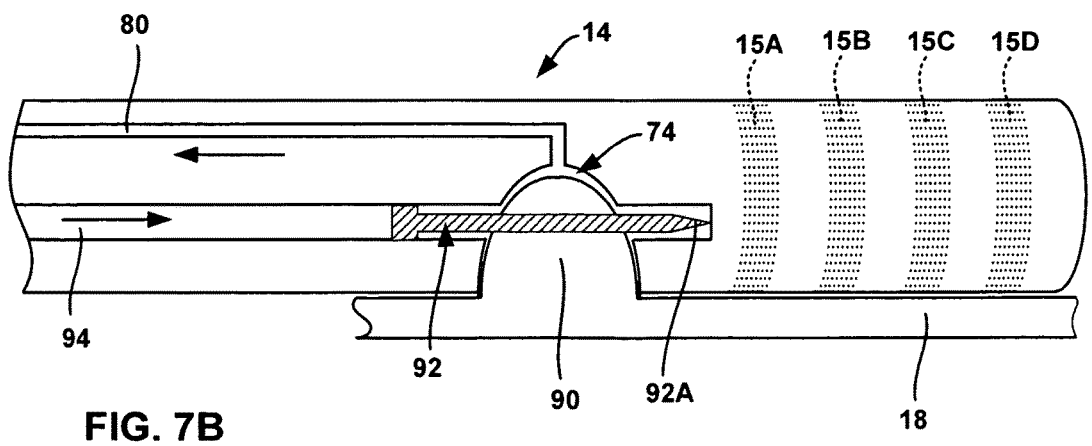

FIGS. 7A and 7B are schematic diagrams illustrating cross-sectional side views of lead 14 taken along line B to B' in FIG. 5. FIGS. 7A and 7B show attachment of lead 14 to a tissue proximate to target stimulation site 18. In particular, FIG. 7A illustrates lead 14 during application of suction to target stimulation site 18 to draw tissue 90 adjacent to vacuum cavity 74 into vacuum cavity 74. FIG. 7B illustrates the fixing of lead 14 to tissue 90 of target stimulation site 18. Electrodes 15 are shown in FIGS. 7A-B in phantom lines.

As illustrated in FIG. 7A, lead 14 includes a vacuum channel 80. As described above, vacuum channel 80 extends from proximal end 14A of lead 14 toward distal end 14B of lead 14 and terminates at vacuum cavity 74. Vacuum channel 80 may, for example, comprise a tube or a lumen that extends the length of lead 14. In one embodiment, vacuum channel 80 may be formed in a stylet port (not shown in FIG. 7A) of lead 14. A proximal end (not shown in FIG. 7A) of vacuum channel 80 couples to vacuum 42 (FIG. 2). A distal end 80A of vacuum channel 80 is in fluidic communication with vacuum cavity 74. As described above, vacuum 42 applies suction (as indicated by arrow 81) to vacuum cavity 74 via vacuum channel 80 to draw tissue 90 into vacuum cavity 74. Thus, vacuum channel 80 permits a clinician to draw, and thereby capture, tissue 90 proximate to target stimulation site 18 within vacuum cavity 74.

Lead 14 also includes a fixation element 92 that engages with tissue 90 captured within vacuum cavity 74 to fix lead 14 to tissue 90. In the embodiment illustrated in FIG. 7A-B, fixation element 92 is a fixation pin that is driven through tissue 90 within vacuum cavity 74. The size of fixation element 92 typically depends upon the size of vacuum cavity 74 because it is desirable for fixation element 92 to sufficiently penetrate tissue 90 and sufficiently engage with tissue 90 to fix lead 14 to tissue 90. The larger the size of vacuum cavity 74, the greater the volume of captured tissue 90 within vacuum chamber 74. Accordingly, the size of fixation element 92 increases with an increase in the size of vacuum cavity 74 in order to provide a fixation element 92 that may sufficiently engage with a greater volume of captured tissue 90.

In the embodiment illustrated in FIGS. 7A-B, fixation element 92 is located within a positive pressure line 94. Positive pressure line 94, like vacuum channel 80, may be composed of a tube or lumen and extends from proximal end 14A of lead 14 toward distal end 14B of lead 14 and terminates at vacuum cavity 74. Positive pressure line 94 is coupled to a positive pressure source (not shown) at a proximal end of positive pressure line 94. A distal end of positive pressure line 94 enters into vacuum cavity 74 via opening 84 (FIG. 6).

Positive pressure line 94 permits the physician to apply a positive pressure (as indicated by arrow 95) to drive fixation element 92 through tissue 90 of target stimulation site 18. In this way, fixation element 92 engages with tissue 90 and fixes lead 14 to target stimulation site 18, as shown in FIG. 7B. The physician may apply the positive pressure via positive pressure line 94 in a number of different manners. In one example, the physician may apply the positive pressure by applying a pulse of high pressure fluid, such as a liquid or a gas, to drive fixation element through tissue 90. The pressure of the fluid should be selected to provide fixation element 92 with enough force to penetrate into tissue 90. Fixation element 92 may have a sharp point 92A in order to facilitate the penetration of fixation element 92 into tissue 90.

Friction between fixation element 92 and tissue 90 enables fixation element 92 to remain engaged with tissue 90, and tissue 90 remains in vacuum chamber 74, even if the vacuum is removed from vacuum channel 80. In addition, fixation element 92 may be held engaged with tissue 90 via a positive fixation (e.g., a lock) mechanism.

Positive pressure line 94 may be completely sealed and filled with a biocompatible fluid, such as water, saline solution or air. The proximal end of positive pressure line 94 may be sealed with, for example, silicone seal-sealing ports. Fixation element 92, or a head on fixation element 92, seals the distal end of positive pressure line 94. Fixation element 92 is generally able to move within positive pressure line 94 much like a piston. Force to push fixation element 92 through tissue 90 of target stimulation site 18 captured in vacuum cavity 74 is created by application of a pulse of increased fluid pressure within positive pressure line 94. For example, the physician may control a positive pressure source via control handle attached to positive pressure line 94 of lead 14. This simple delivery method may provide high levels of force, allow multiple curves and bends in lead 14, and enable positive pressure line 94 to be formed in many shapes and sizes.

In another example, a flexible, but generally incompressible, wire may be placed within positive pressure line 94 and used as a push rod to force fixation element 92 through the captured tissue 90 of target stimulation site 18. Alternatively, the wire may be used as a pull wire to pull fixation element 92 through captured tissue 90 of target stimulation site 18. This wire presents compressive force from a control handle coupled to the wire directly to fixation element 92. This method may eliminate any safety risk of pressurized fluids entering patient 12 or, in some embodiments, permit retraction of fixation element 92 after an unsuccessful fixation attempt. Moreover, the flexible wire may be attached to fixation element 92 and pulled back to remove fixation element 92 from tissue 90 for easy removal of lead 14 from patient 16 during an explanation procedure or for adjusting a position of lead 14.

Fixation element 92 may be made from, for example, stainless steel, titanium, Nitinol, other shape memory materials, a high density polymer, or other biocompatible material. The shaft of fixation element 92 may be smooth or rough, and the tip may have a sharp point 92A to allow for easy penetration into tissue. Fixation element 92 may be driven tissue 90 under pressure or upon actuation by a push rod. In another embodiment, lead 14 may be attached without the use of a penetrating rod but with a spring-loaded clip to pinch tissue 90 within vacuum cavity 74. A variety of other attachment mechanisms, such as pins, clips, barbs, sutures, helical screws, surgical adhesives, and the like may be used to attach lead 14 to tissue 90 of target stimulation site 18.

Figure 8A:
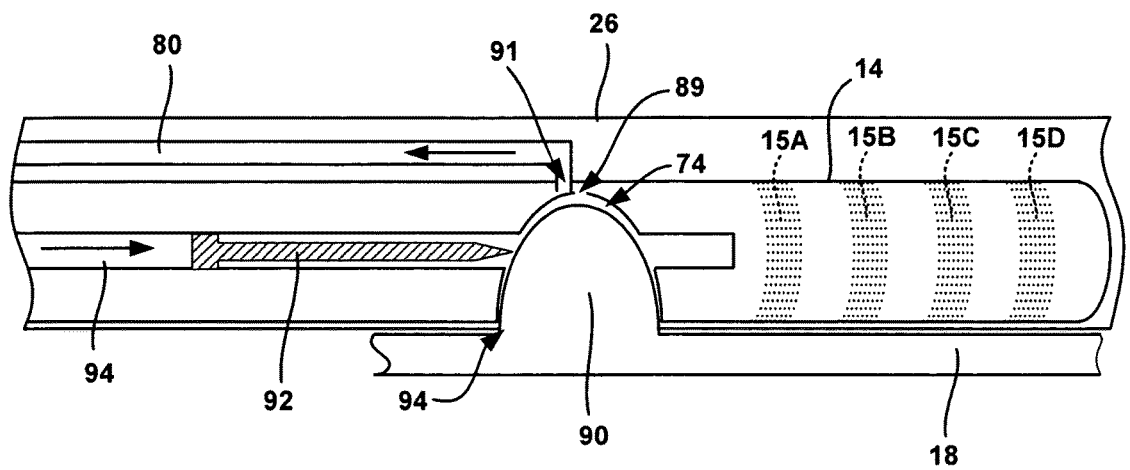
FIGS. 8A and 8B are schematic diagrams illustrating cross-sectional side views of a lead and an introducer needle taken along line B to B' in FIG. 5.
Figure 8B:
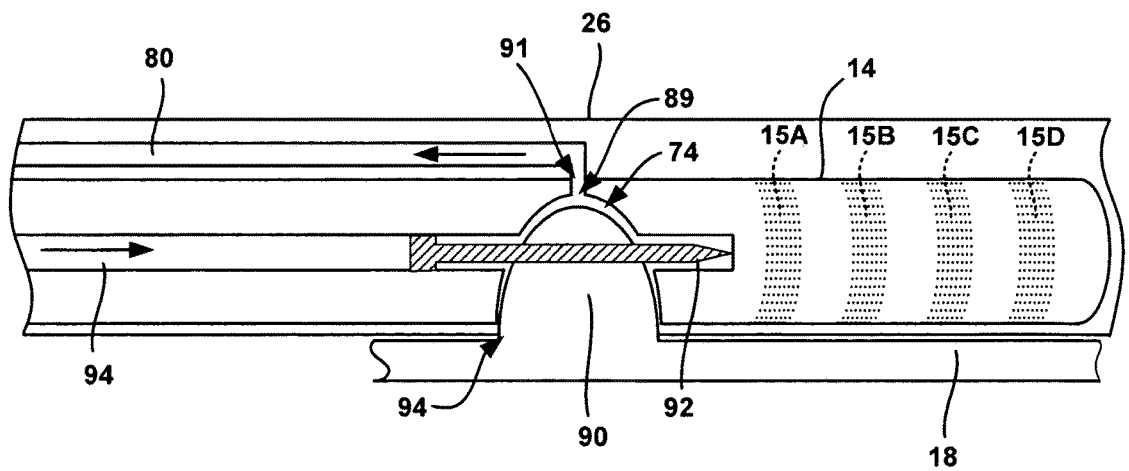

FIGS. 8A and 8B illustrate schematic cross-sectional side views of lead 14 and introducer needle 26 taken along line B to B' in FIG. 5. FIGS. 8A and 8B conform substantially to FIGS. 7A and 7B, but vacuum channel 80 is located within introducer needle 26 instead of within lead 14.

Vacuum channel 80 within introducer needle 26 couples to vacuum 42 at a proximal end and is in fluidic communication with vacuum cavity 74 of lead 14. In particular, vacuum cavity 74 may define vacuum inlet 89, which permits fluidic communication between outlet 91 of vacuum channel 80 and vacuum cavity 74. In FIG. 8A, lead 14 has been introduced into introducer 26 such that outlet 91 of vacuum channel 80 does not align with vacuum inlet 89 of vacuum cavity 74. However, as FIG. 8B illustrates, either lead 14 or introducer 26 may be adjusted to align outlet 91 of vacuum channel 80 with vacuum inlet 89 of vacuum cavity 74 and fluidically connect vacuum channel 80 and vacuum cavity 74. Proper alignment between lead 14 and introducer 26 for achieving fluidic communication between outlet 91 of vacuum channel 80 with vacuum inlet 89 of vacuum cavity 74 may be aided by visible markers on lead body 70 and introducer 26. For example, both introducer 26 and lead body 70 may each include a marker (e.g., a printed line, indentation in lead body 70, a radiographic marker or another suitable visible marker). Aligning the markers on introducer 26 and lead body 70 with each other aligns outlet 91 of vacuum channel 80 with vacuum inlet 89 of vacuum cavity 74. Thus, a clinician may visually confirm that vacuum source 42 is in fluidic communication with vacuum cavity 74 in lead body 70.

The location of the coupling between vacuum channel 80 and vacuum cavity 74 is sealed to allow the suction of vacuum 42 (FIG. 2) to be applied to vacuum cavity 74. In this manner, vacuum channel 80 within introducer needle 26 couples vacuum 42 to the vacuum cavity within lead 14.

Introducer needle 26 may also include an opening 94 within the body of introducer needle 26 that aligns with vacuum cavity 74. The suction applied by vacuum 42 draws tissue 90 proximate to target stimulation site 18 into vacuum cavity 74 through opening 94 within the body of introducer needle 26. In one embodiment, opening 94 may be covered by a membrane mounted over opening 94 during placement of introducer needle 26. The membrane covering opening 94 may be ruptured upon application of suction from vacuum 42, thus allowing tissue 90 to enter vacuum cavity 74.

In another embodiment, introducer needle 26 may not include opening 94. Instead, introducer needle 26 may be slightly retracted to expose vacuum cavity 74 of lead 14 to target stimulation site 18. Vacuum 42 may then apply suction to draw tissue 90 into vacuum cavity 74, and attach lead 14 to tissue 90 using fixation element 92 as described in detail above.

FIGS. 9A-E illustrates a schematic cross-sectional side view of another exemplary lead 100. Lead 100 conforms substantially to lead 14 of FIGS. 7A-B, but lead 100 includes a plurality of vacuum cavities. In particular, lead 100 includes vacuum cavities 74A and 74B (collectively "vacuum cavities 74"). In the example illustrated in FIG. 9, vacuum cavities 74A and 74B are lined up substantially adjacent to one another.

Lead 100 also includes a vacuum channel 102. A distal end of vacuum channel 102 splits into two branches proximate to vacuum cavities 74. The first branch of vacuum channel 102 is in fluidic communication with vacuum cavity 74A and the second branch of vacuum channel 102 is in fluidic communication with vacuum cavity 74B. Each of the branches provides suction (as indicated by arrow 103) from vacuum 42 to the respective one of vacuum cavities 74 to draw in respective portions of tissue 90A and 90B from target stimulation site 18. In one embodiment, vacuum cavities 74 are located closely enough together that tissue is drawn into each of the vacuum cavities 74 substantially simultaneously. Although only a single vacuum channel 102 is illustrated in FIG. 9, each of vacuum cavities 74 may be coupled to separate vacuum channels. In this manner, the physician may selectively apply suction to the vacuum channels.

Upon drawing tissue into vacuum cavities 74, a positive pressure (as indicated by arrow 95) is applied via positive pressure line 94 to drive fixation element 92 through tissue 90A and 90B of target stimulation site 18. Thus, in the embodiment illustrated in FIG. 9, a single fixation element 92 is used to fix tissue 90A and 90B to lead 100. In other words, fixation element 92 has a sufficient length to pierce through both portions of tissue 90A and 90B. Alternatively, lead 100 may include a pair of fixation elements that each fix the tissue in the respective vacuum cavities 74. For example, a first fixation element may be driven through tissue 90A in vacuum cavity 74A and a second fixation element may be driven through tissue 90B in vacuum cavity 74B. To this end, lead 100 may also include more than one positive pressure line.

Figure 9A:
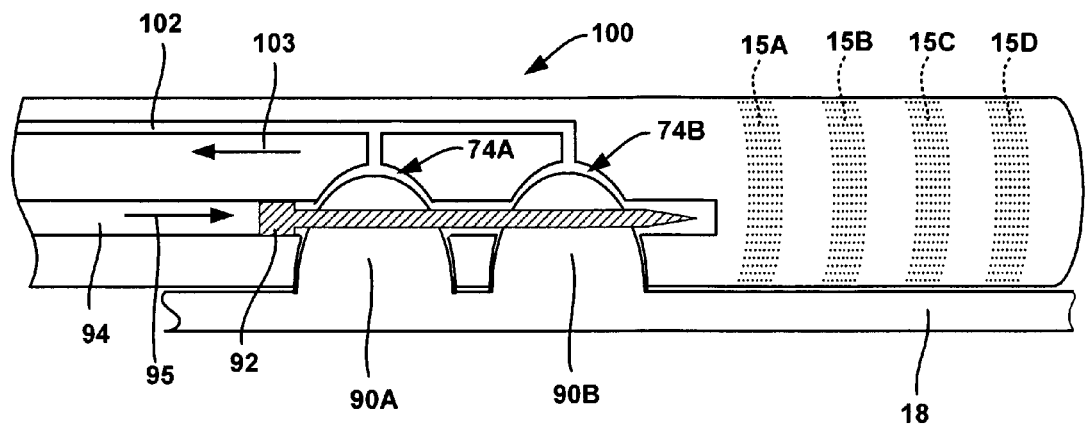
FIG. 9A is a schematic diagram illustrating a cross-sectional side view of another exemplary lead, which includes two vacuum chambers.
Figure 9B:
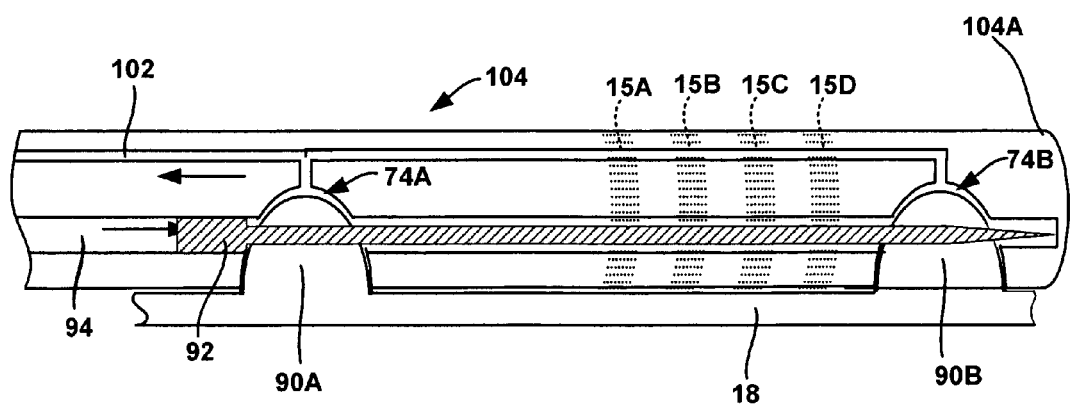
FIGS. 9B-9E illustrate alternate locations for vacuum chambers of a lead.

In other embodiments, a lead may include any number of vacuum cavities 74 arranged in different ways. FIGS. 9B-9E illustrate other possible arrangements for vacuum cavities 75. FIG. 9B illustrates a schematic cross-sectional view of lead 104, which includes vacuum cavity 74A located proximate to electrodes 15 and vacuum cavity 74B located between distal end 104A of lead 104 and electrodes 15. In FIG. 9B, both vacuum channel 102 and positive pressure line 94 are disposed within lead 104 and extend past electrodes 15 in order to allow fluidic communication with both vacuum cavities 74A and 74B. Vacuum channel 102 and positive pressure line 94 may be routed through lead body 101 so that they do not interfere with conductors 82 (FIG. 6) that electrically connect electrodes 15 to neurostimulator 12 (FIG. 1) or a lead extension. Alternatively, vacuum channel 102 and/or positive pressure line 94 may be disposed within introducer 26 (FIG. 1) or otherwise disposed outside of lead 100.

Lead 104 may be useful for locally fixing distal end 104A of lead 104. In some applications of therapy system 10 (FIGS. 1A and 2), such as when therapy system 10 is used to stimulate a pudendal nerve, it may be desirable to locally fix distal end 104A of lead 104.

Figure 9C:
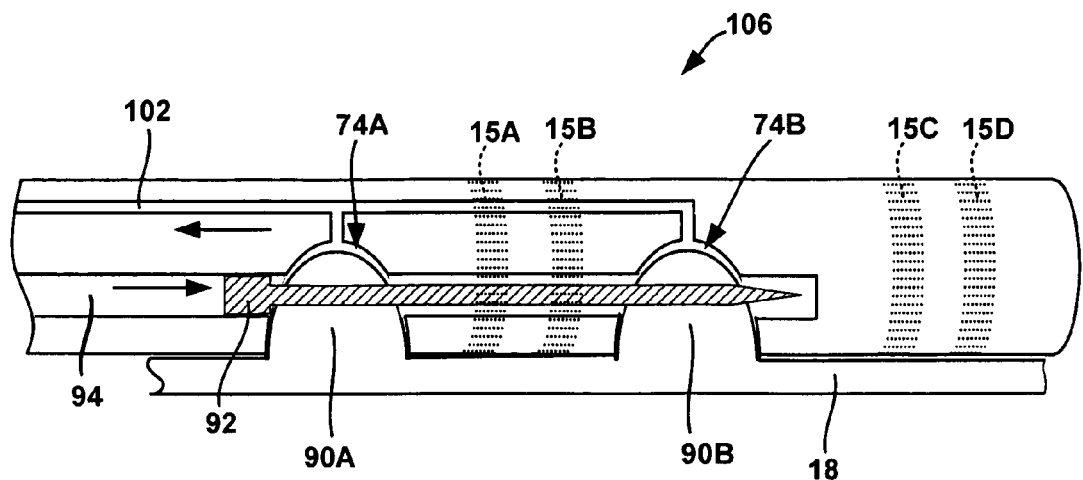
Figure 9D:
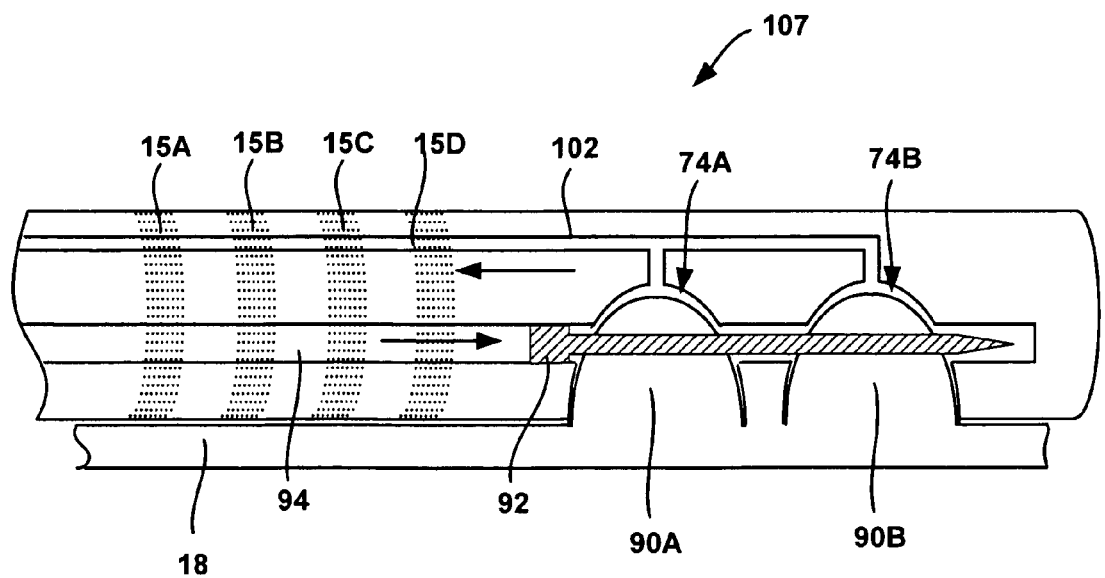

In another embodiment, vacuum cavities 74A and 74B may be located between electrodes 15, as shown in FIG. 9C with respect to lead 106. Fixing lead 106 between electrodes 15 may help draw tissue 90 closer to electrodes, and may also be useful for locally fixing electrodes 15. In yet another embodiment, vacuum cavities 74A and 74B may be located between electrodes 15 and a distal end of a lead, as shown in FIG. 9D with respect to lead 107.

Figure 9E:
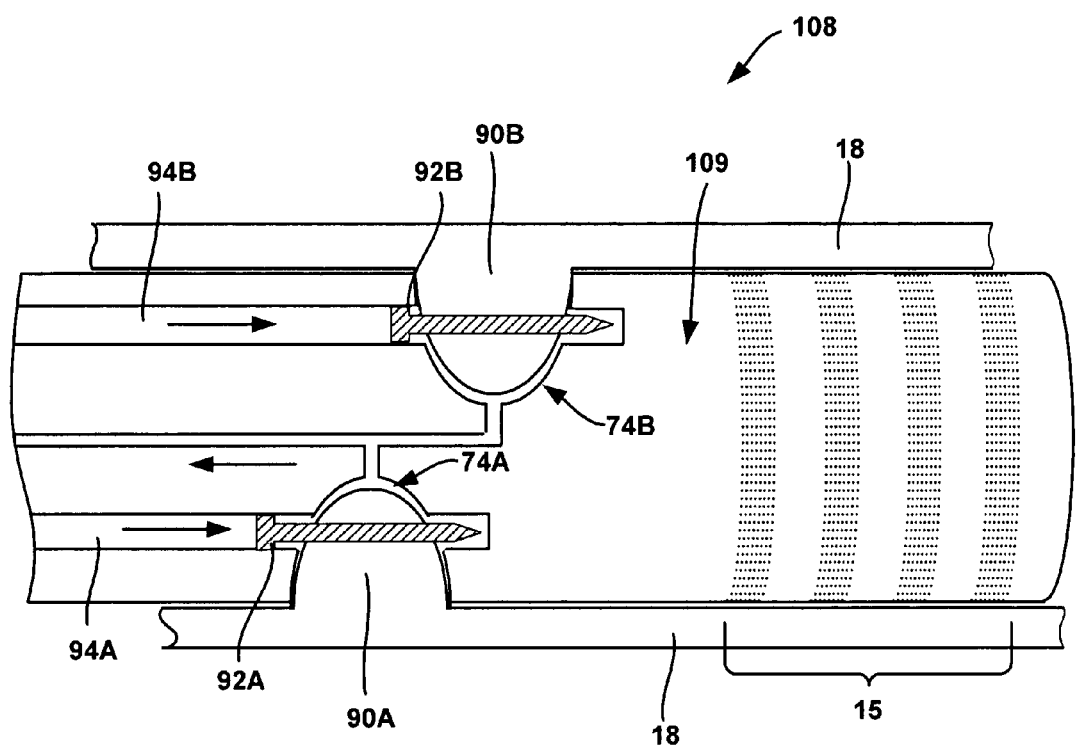

Vacuum cavities 74A and 74B may also be on opposite sides of a lead body, as shown in FIG. 9E with respect to lead 108. Lead 108 includes lead body 109, which has a circular cross-section (in an axial direction). Lead body 109 defines vacuum cavities 74A and 74B on radially opposite sides of lead body 109. Vacuum channel 102 is centrally located in order to accommodate the different radial locations of vacuum cavities 74A and 74B. However, lead 108 includes two positive pressure lines 94A and 94B, which are fluidically connected to vacuum cavities 74A and 74B, respectively. Disposed within each positive pressure line 94A and 94B are fixation elements 92A and 92B, respectively, which each engage with tissue 90A and 90B that is received by the respective vacuum cavities 74A and 74B.

While fixing lead 108 at two different radial locations may be useful in some applications, in other applications, it may also be useful to fix lead 108 at one radial location or along one portion of lead body 109. For example, as described in commonly-assigned U.S. patent application Ser. No. 11/591,279 by Martin T. Gerber, entitled, "IMPLANTABLE MEDICAL ELONGATED MEMBER INCLUDING FIXATION ELEMENTS ALONG AN INTERIOR SURFACE," which was filed on the same date as the present disclosure, issued as U.S. Pat. No. 8,688,238 on Apr. 1, 2014, and is incorporated herein by reference in its entirety, fixing lead 108 such that vacuum cavities 74A and 74B face away from an epidermis layer of patient 16 when lead 108 is implanted in patient 16 may be useful in a occipital nerve stimulation application, such as the one shown in FIG. 1. For example, fixing lead 108 along the "interior surface" (i.e., the surface facing away from the scalp of patient 16) may help minimize irritation to patient 16 from lead 108 and/or damage to the scalp of patient 16.

Figure 10:
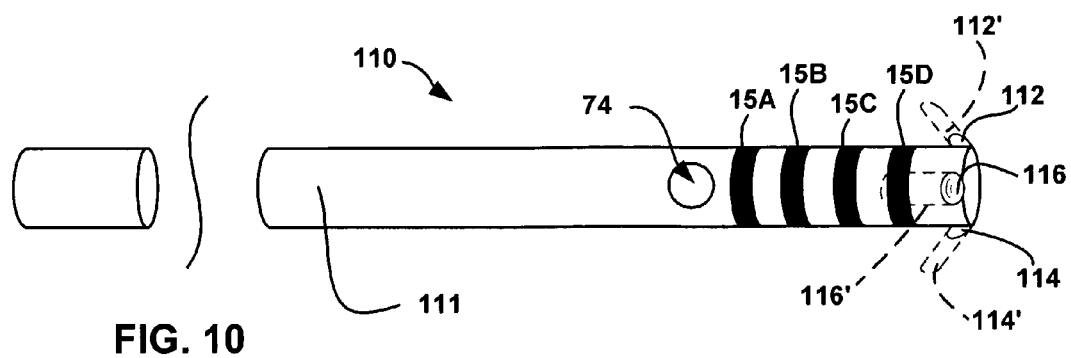
FIG. 10 is a schematic diagram illustrating an exemplary lead that utilizes the fixation techniques of this disclosure in conjunction with other fixation techniques.
Figure 11:
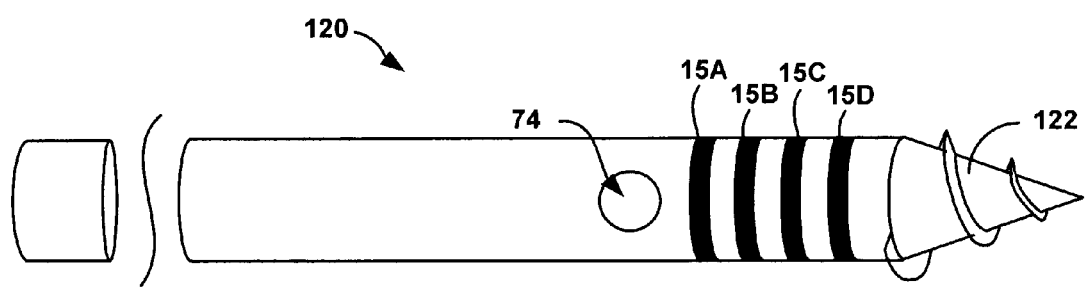
FIG. 11 is a schematic diagram illustrating another exemplary lead that utilizes the fixation techniques of this disclosure in conjunction with other fixation techniques.

FIG. 10 and FIG. 11 are schematic diagrams illustrating exemplary leads that utilize the fixation techniques of this disclosure in conjunction with other fixation techniques. In particular, FIG. 10 illustrates a lead 110 that includes hydrogel fixation members 112, 114, and 116 in addition to vacuum cavity 74. Hydrogel fixation members 112, 114 and 116 may be mounted to lead body 11 to aid in the attachment of lead 110 to tissue surrounding lead 110. During implantation of lead 110 in patient 16, hydrogel fixation members 112, 114, and 116 are in a first, substantially dehydrated state. Upon implantation in patient 16, hydrogel fixation members absorb fluid (e.g., water) from surrounding tissue and expand to a second, substantially hydrated state, which is indicated in FIG. 10 in phantom lines (and designated hydrogel fixation members 112', 114', and 116'). In the embodiment shown in FIG. 10, hydrogel fixation members 112, 114, and 116 are mounted at distal end of lead 110. In other embodiments, hydrogel fixation members 112, 114, and 116 may be otherwise arranged with respect to lead body 111.

Examples of suitable hydrogel fixation elements are described in commonly assigned U.S. Patent Application Publication No. 2006/0095077, entitled "EXPANDABLE FIXATION STRUCTURES and filed on Oct. 29, 2004, U.S. Patent Application Publication No. 2006/0095078, entitled "EXPANDABLE FIXATION MECHANISM" and filed on Oct. 29, 2004, and U.S. patent application Ser. No. 11/591,174 by Martin T. Gerber, entitled "IMPLANTABLE MEDICAL ELONGATED MEMBER INCLUDING EXPANDABLE FIXATION MEMBER" and filed on the same date as the present disclosure and published as U.S. Patent Application Publication No. 2008/0103576 on May 1, 2008, which are each incorporated herein by reference in their entirety.

FIG. 11 illustrates a lead 120 that includes a threaded fixation structure 122 in addition to vacuum cavity 74. Threaded fixation structure 122 may be attached to tissue at the distal end of lead 120 to aid vacuum cavity 74 in attachment of lead 122 to tissue surrounding lead 122. An example of a suitable threaded fixation structures is described in commonly-assigned U.S. patent application Ser. No. 11/591,171 by Martin T. Gerber, entitled "IMPLANTABLE MEDICAL LEAD WITH THREADED FIXATION", filed on the same date as the present disclosure, published as U.S. Patent Application Publication No. 2008/0103572 on May 1, 2008, and incorporated herein by reference in its entirety.

The techniques of this disclosure may be utilized in conjunction with other lead fixation techniques. For example, each of leads 14, 100, 104, 106, 107, and 108 of FIGS. 5 and 9A-E, respectively, may also include other actively or passively deployed fixation element that helps prevent migration of the lead when the lead is implanted in patient 16, such as, but not limited to, one or more tines, barbs, hooks, wire-like elements, adhesives (e.g., surgical adhesives), balloon-like fixation elements, collapsible or expandable fixation structures, and so forth. Fixation elements 50, 52, and 54 may be composed of any suitable biocompatible material, including, but not limited to, titanium, stainless steel, Nitinol, other shape memory materials, hydrogel or combinations thereof.

Other suitable fixation elements may include wire-like fixation elements as described in commonly assigned U.S. Patent Application Publication No. 2005/0096718, entitled "IMPLANTABLE STIMULATION LEAD WITH FIXATION MECHANISM" and filed on Oct. 31, 2003 and commonly-assigned U.S. patent application Ser. No. 11/591,447 by Martin T. Gerber, entitled "IMPLANTABLE MEDICAL ELONGATED MEMBER INCLUDING BALOON FIXATION ELEMENT" and filed on the same date as the present disclosure, and published as U.S. Patent Application Publication No. 2008/0103575 on May 1, 2008. An example of tine fixation elements is described in U.S. Pat. No. 6,999,819, entitled "IMPLANTABLE MEDICAL ELECTRICAL STIMULATION LEAD FIXATION METHOD AND APPARATUS" and filed on Nov. 9, 2001.

An example of a suitable in situ formed fixation element is described in commonly-assigned U.S. patent application Ser. No. 11/591,433 by Martin T. Gerber, entitled, "IMPLANTABLE MEDICAL ELONGATED MEMBER WITH IN SITU FORMED FIXATION ELEMENT" and filed on the same date as the present disclosure, and published as U.S. Patent Application Publication No. 2008/0103578 on May 1, 2008. An example of suitable adhesive fixation elements are described in commonly-assigned U.S. patent application Ser. No. 11/591,443 by Martin T. Gerber, entitled, "IMPLANTABLE MEDICAL ELONGATED MEMBER WITH ADHESIVE ELEMENTS" and filed on the same date as the present disclosure, and issued as U.S. Pat. No. 9,643,004 on May 9, 2017. An example of suitable balloon-like fixation elements are described in commonly-assigned U.S. patent application Ser. No. 11/591,447 by Martin T. Gerber, entitled, "IMPLANTABLE MEDICAL ELONGATED MEMBER INCLUDING BALLOON FIXATION ELEMENT" and filed on the same date as the present disclosure, and published as U.S. Patent Application Publication No. 2008/0103575 on May 1 2008.

Each of the aforementioned patents and patent applications relating to suitable fixation elements are incorporated herein by reference in their entirety.

Figure 12:
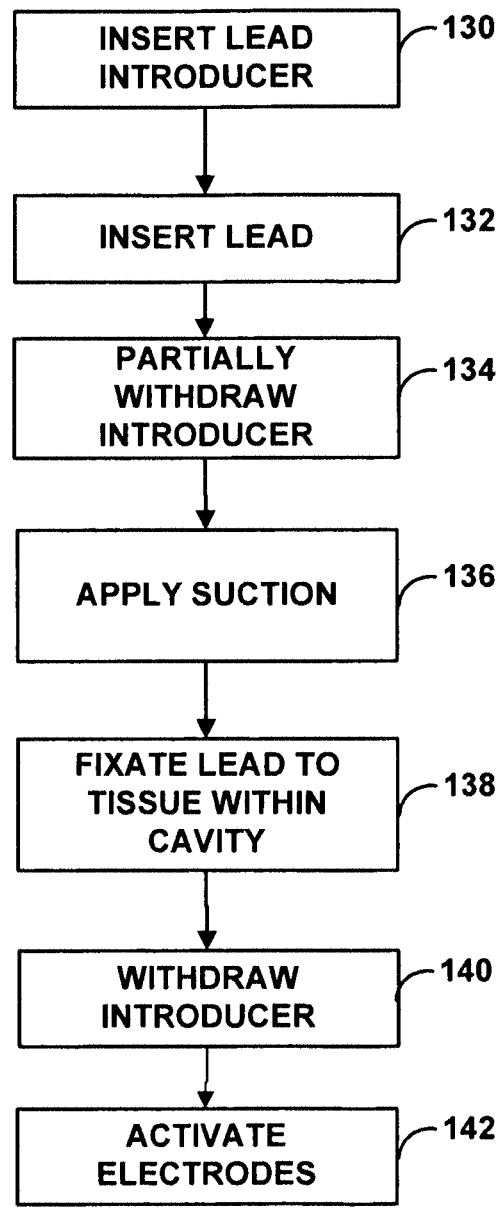
FIG. 12 is a flow diagram illustrating exemplary implantation of a lead.

FIG. 12 is a flow diagram illustrating exemplary implantation of a lead, such as lead 14 of FIG. 1. Initially, a lead introducer, such as introducer needle 26 of FIG. 1, is introduced and advanced to a target stimulation site 18 within patient 16 (130). Once introducer needle 26 is fully inserted, lead 14 may be advanced through introducer needle 26 and positioned at target stimulation site 18 (132).

Once lead 14 is positioned at target stimulation site 18, introducer needle 26 is partially removed to expose the distal end of lead 14 and, more particularly, to expose vacuum cavity 74 (134). A vacuum 42 applies suction to at least one vacuum cavity 74 to draw tissue surrounding lead 14 into vacuum cavity 74 (136). Lead 14 is fixated to the tissue drawn into vacuum cavity 74 by a fixation element (138). For example, a positive pressure may be used to drive a fixation pin through the tissue drawn into vacuum cavity 74.

After fixing lead 14 to the target stimulation site, introducer needle 26 may be completely withdrawn from patient 16 and electrodes 15 of lead 14 may be activated to provides therapy to target stimulation site 18 (140, 142). For example, proximal end 14A of lead 14, and in particular electrical contacts on the proximal end 14A of lead 14A, may be electrically coupled to neurostimulator 12 (FIG. 1), which may deliver electrical stimulation therapy to target stimulation site 18 via electrode 15. Proximal end 14A of lead 14A may be directly coupled to neurostimulator 12 or may be coupled to a lead extension which is coupled to neurostimulator.

A lead including a vacuum cavity and fixation element for fixing the lead to surrounding tissue may be useful for various electrical stimulation systems. For example, the lead may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. In addition, the fixation technique described herein may also be useful for fixing a catheter, such as a drug deliver catheter, proximate to a target drug delivery site.

Although the techniques of this disclosure are described with reference to neurostimulation, the techniques may be useful in systems that provide other types of therapy to target therapy delivery sites. For example, the techniques may be applicable for systems that deliver electrical stimulation therapy to one or more muscles of a patient, e.g., a heart. Moreover, the techniques may also be useful for delivering fluid therapy to a target delivery site via a catheter. Various embodiments have been described in this disclosure. These and other embodiments are within the scope of the following claims.

The invention claimed is:

1. An implantable medical elongated member configured to deliver a therapy from a medical device to a target therapy delivery site in a patient, the implantable elongated member comprising:
    an elongated body extending between a proximal end configured to couple to the medical device and a distal end;
    a vacuum cavity defined by the elongated body and configured to receive vacuum pressure from a vacuum source to draw tissue of the patient into the vacuum cavity, wherein the vacuum cavity defines at least a first opening and a second opening;
    a positive pressure line disposed within the elongated body and connected to the vacuum cavity via the first opening;
    a fixation element disposed within the positive pressure line, wherein the fixation element is configured to enter the vacuum cavity from the positive pressure line through the first opening when a positive pressure is exerted on the fixation element via the positive pressure line; and
    a vacuum channel disposed within the elongated body to couple the vacuum cavity to the vacuum source, wherein the vacuum channel is connected to the vacuum cavity via the second opening,
    wherein the elongated member comprises a catheter.

2. The implantable medical elongated member of claim 1, wherein the elongated body comprises one or more electrodes.

3. The implantable elongated member of claim 2, wherein the vacuum cavity is located between the one or more electrodes and a proximal end of the elongated body.

4. The implantable medical elongated member of claim 2, wherein the elongated body comprises two or more electrodes, and wherein the vacuum cavity is located between a first electrode of the two or more electrodes and a second electrode of the two or more electrodes.

5. The implantable elongated member of claim 2, wherein the vacuum cavity is located between the one or more electrodes and a distal end of the elongated body.

6. The implantable medical elongated member of claim 1, wherein the vacuum cavity comprises a first vacuum cavity and a second vacuum cavity, wherein the first and second vacuum cavities are each configured to receive tissue adjacent to the respective first and second vacuum cavities.

7. The implantable medical elongated member of claim 6, wherein the fixation element is configured to enter both the first and second vacuum cavities when the positive pressure is exerted on the fixation element via the positive pressure line.

8. The implantable medical elongated member of claim 1, further comprising a vacuum inlet proximate to the vacuum cavity configured to couple to an introducer vacuum channel within an introducer to place the vacuum cavity in fluidic communication with the vacuum source.

9. The implantable medical elongated member of claim 1, wherein the fixation element comprises one of a pin or a screw.

10. The implantable medical elongated member of claim 1, wherein the fixation element comprises a proximal end and a distal end, wherein the elongated body defines a space configured to receive the distal end of the fixation element when the fixation element extends through the vacuum cavity.

11. The implantable medical elongated member of claim 10, wherein when the fixation element extends through the vacuum cavity, the proximal end of the fixation element is disposed within the positive pressure line and the distal end is disposed within the space defined by the elongated body.

12. A system comprising:
    a medical device; and
    an implantable medical elongated member configured to deliver a therapy from the medical device to a target therapy delivery site in a patient, the implantable elongated member comprising:
        an elongated body extending between a proximal end configured to couple to the medical device and a distal end;
        a vacuum cavity defined by the elongated body and configured to receive vacuum pressure from a vacuum source to draw tissue of the patient into the vacuum cavity, wherein the vacuum cavity defines at least a first opening and a second opening;
        a positive pressure line disposed within the elongated body and connected to the vacuum cavity via the first opening;
        a fixation element disposed within the positive pressure line, wherein the fixation element is configured to enter the vacuum cavity from the positive pressure line through the first opening when a positive pressure is exerted on the fixation element via the positive pressure line; and
        a vacuum channel disposed within the elongated body to couple the vacuum cavity to the vacuum source, wherein the vacuum channel is connected to the vacuum cavity via the second opening,
        wherein the elongated member comprises a catheter.

13. The system of claim 12, further comprising:
    the vacuum source; and
    an introducer including an introducer vacuum channel to couple to the vacuum source, wherein the elongated body includes a vacuum inlet in fluidic communication with the vacuum cavity to couple the vacuum cavity to the introducer vacuum channel.

14. The system of claim 13, further comprising a first marker on the elongated body and a second marker on the introducer to align with the first marker on the elongated body to align the vacuum inlet of the elongated body with the introducer vacuum channel.

15. The system of claim 12, further comprising:
the vacuum source.

16. The system of claim 12, wherein the vacuum cavity comprises a first vacuum cavity and a second vacuum cavity, wherein the first and second vacuum cavities are each configured to receive tissue adjacent to the respective first and second vacuum cavities.

17. The system of claim 12, wherein the fixation element comprises one of a pin or a screw.

18. The system of claim 12, wherein the elongated body comprises at least one electrode.

19. The system of claim 12, wherein the medical device comprises at least one of a sensor to sense a parameter of a patient, an electrical stimulator or a fluid delivery device.

20. A method comprising:
inserting an implantable medical elongated member into a patient, the implantable medical elongated member comprising:
an elongated body extending between a proximal end configured to couple to the medical device and a distal end;
a vacuum cavity defined by the elongated body and configured to receive tissue of the patient, wherein the vacuum cavity defines at least a first opening and a second opening;
a positive pressure line disposed within the elongated body and connected to the vacuum cavity via the first opening;
a fixation element disposed within the positive pressure line; and
a vacuum channel disposed within the elongated body and connected to the vacuum cavity via the second opening,
wherein inserting the introducer into the patient comprises subcutaneously introducing the introducer proximate to a peripheral nerve of the patient, wherein inserting the implantable medical elongated member into a patient comprises introducing an introducer into the patient and introducing the implantable medical elongated member into the introducer, and wherein inserting the introducer into the patient comprises subcutaneously introducing the introducer proximate to a peripheral nerve of the patient;
advancing the implantable medical elongated member to a target therapy delivery site within the patient;
applying negative pressure via the vacuum channel to the vacuum cavity of the implantable medical elongated member to draw tissue adjacent to the vacuum cavity into the vacuum cavity; and
applying a positive pressure to the fixation element via the positive pressure line to advance the fixation element from the positive pressure line, into the vacuum cavity, and into engagement with the tissue within the vacuum cavity to fix the implantable medical elongated member to the tissue.

21. The method of claim 20, further comprising coupling the implantable medical elongated member to a medical device, the medical device configured to deliver a therapy to the target therapy delivery site via the implantable medical elongated member.

22. The method of claim 21, wherein the medical device is at least one of an electrical stimulator, a sensor or a fluid delivery device.

23. The method of claim 20, wherein inserting the introducer proximate to the peripheral nerve comprises positioning the introducer substantially transversely across an occipital nerve.

24. An implantable medical lead comprising:
a lead body extending between a proximal end and a distal end;
one or more electrodes proximate to the distal end of the lead body;
a vacuum channel disposed within the lead body;
a vacuum cavity defined by the lead body and configured to receive vacuum pressure from a vacuum source via the vacuum channel to draw tissue of the patient into the vacuum cavity, wherein the vacuum cavity defines at least a first opening and a second opening, and wherein the vacuum channel connects to the vacuum cavity via the first opening;
a positive pressure line disposed within the lead body and connected to the vacuum cavity via the second opening; and
a fixation element disposed within the positive pressure line and configured to enter the vacuum cavity from the positive pressure line when a positive pressure is exerted on the fixation element via the positive pressure line,
wherein the vacuum cavity comprises a first vacuum cavity located between the one or more electrodes and the proximal end of the lead body and a second vacuum cavity located between the one or more electrodes and the distal end of the lead body.

* * * * *